US012778654B2

(12) United States Patent
Ransbury et al.

(10) Patent No.: US 12,778,654 B2
(45) Date of Patent: Nov. 3, 2026

(54) SYSTEMS AND METHODS FOR LESION FORMATION AND ASSESSMENT

(71) Applicant: 460Medical, Inc., Weston, MA (US)

(72) Inventors: Terrance J. Ransbury, Chapel Hill, NC (US); Omar Amirana, Weston, MA (US)

(73) Assignee: 460Medical, Inc., Weston, MA (US)

( * ) Notice: Subject to any disclaimer, the term of this patent is extended or adjusted under 35 U.S.C. 154(b) by 0 days.

(21) Appl. No.: 17/387,915

(22) Filed: Jul. 28, 2021

(65) Prior Publication Data

US 2022/0031377 A1 Feb. 3, 2022

Related U.S. Application Data

(60) Provisional application No. 63/057,569, filed on Jul. 28, 2020.

(51) Int. Cl.
*A61B 18/00* (2006.01)
*A61B 1/04* (2006.01)
(Continued)

(52) U.S. Cl.
CPC .............. *A61B 18/00* (2013.01); *A61B 1/043* (2013.01); *A61B 1/07* (2013.01); *A61B 5/14546* (2013.01);
(Continued)

(58) Field of Classification Search
CPC ........... A61B 18/00; A61B 1/043; A61B 1/07; A61B 5/14546; A61B 5/1459; A61B 8/12; A61B 8/4416; A61B 2018/00577; A61B 2018/00904; A61B 2018/00982; A61B 2018/00434; A61B 2018/00511; A61B 2562/0204; A61B 2562/0271; A61B 1/0011; A61B 1/00165; A61B 1/00181; A61B 1/042; A61B 1/0625; A61B 1/063;
(Continued)

(56) References Cited

U.S. PATENT DOCUMENTS

| | | | |
|---|---|---|---|
| 3,387,305 | A | 6/1968 | Shafer |
| 3,831,467 | A | 8/1974 | Moore |

(Continued)

FOREIGN PATENT DOCUMENTS

| | | |
|---|---|---|
| CN | 1289239 | 3/2001 |
| CN | 1764419 | 4/2006 |

(Continued)

OTHER PUBLICATIONS

Anderson et al. "Real-time spectroscopic assessment of thermal damage: implications for radiofrequency ablation". J Gastrointest Surg. 2004; 8: 660-669.

(Continued)

*Primary Examiner* — Serkan Akar
*Assistant Examiner* — Gabriel Victor Popescu
(74) *Attorney, Agent, or Firm* — Greenberg Traurig, LLP; David J. Dykeman; Roman Fayerberg

(57) ABSTRACT

System and methods for optical tissue interrogation are provided. In some embodiments, a catheter for visualizing ablated tissue is provided, and can include a catheter body, and a distal tip positioned at a distal end of the catheter body. The distal tip can have one or more openings for exchange of light energy between the distal tip of the catheter and tissue.

17 Claims, 14 Drawing Sheets

(51) Int. Cl.

| | |
|---|---|
| ***A61B 1/07*** | (2006.01) |
| ***A61B 5/145*** | (2006.01) |
| ***A61B 5/1459*** | (2006.01) |
| ***A61B 8/00*** | (2006.01) |
| ***A61B 8/12*** | (2006.01) |

(52) U.S. Cl.
CPC .............. *A61B 5/1459* (2013.01); *A61B 8/12* (2013.01); *A61B 8/4416* (2013.01); *A61B 2018/00577* (2013.01); *A61B 2018/00904* (2013.01); *A61B 2018/00982* (2013.01)

(58) Field of Classification Search
CPC ... A61B 1/0638; A61B 1/0669; A61B 5/0036; A61B 5/0044; A61B 5/0071; A61B 5/0075; A61B 5/01; A61B 5/6852; A61B 8/445
See application file for complete search history.

(56) References Cited

U.S. PATENT DOCUMENTS

| | | | |
|---|---|---|---|
| 4,024,873 | A | 5/1977 | Antoshkiw et al. |
| 4,619,247 | A | 10/1986 | Inoue et al. |
| 5,074,306 | A | 12/1991 | Green et al. |
| 5,187,572 | A | 2/1993 | Nakamura et al. |
| 5,350,375 | A | 9/1994 | Deckelbaum et al. |
| 5,353,807 | A | 10/1994 | DeMarco |
| 5,419,323 | A | 5/1995 | Kittrell et al. |
| 5,421,337 | A | 6/1995 | Richards-Kortum et al. |
| 5,507,287 | A | 4/1996 | Palcic et al. |
| 5,540,681 | A | 7/1996 | Strul et al. |
| 5,584,799 | A | 12/1996 | Gray |
| 5,590,660 | A | 1/1997 | MacAulay et al. |
| 5,657,760 | A | 8/1997 | Ying et al. |
| 5,681,260 | A | 10/1997 | Ueda et al. |
| 5,713,364 | A | 2/1998 | DeBaryshe et al. |
| 5,749,830 | A | 5/1998 | Kaneko et al. |
| 5,833,688 | A | 11/1998 | Sieben et al. |
| 5,885,258 | A | 3/1999 | Sachdeva et al. |
| 5,904,651 | A | 5/1999 | Swanson et al. |
| 5,908,445 | A | 6/1999 | Whayne et al. |
| 5,954,665 | A | 9/1999 | Ben Haim |
| 6,064,069 | A | 5/2000 | Nakano et al. |
| 6,112,123 | A | 8/2000 | Kelleher et al. |
| 6,124,597 | A | 9/2000 | Shehada et al. |
| 6,174,291 | B1 | 1/2001 | McMahon et al. |
| 6,178,346 | B1 | 1/2001 | Amundson et al. |
| 6,197,021 | B1 | 3/2001 | Panescu et al. |
| 6,208,886 | B1 | 3/2001 | Alfano et al. |
| 6,217,573 | B1 | 4/2001 | Webster et al. |
| 6,219,566 | B1 | 4/2001 | Weersink et al. |
| 6,251,107 | B1 | 6/2001 | Schaer |
| 6,289,236 | B1 | 9/2001 | Koenig et al. |
| 6,309,352 | B1 | 10/2001 | Oraevsky et al. |
| 6,343,228 | B1 | 1/2002 | Qu |
| 6,423,055 | B1 | 7/2002 | Farr et al. |
| 6,423,057 | B1 | 7/2002 | He et al. |
| 6,450,971 | B1 | 9/2002 | Andrus et al. |
| 6,485,413 | B1 | 11/2002 | Boppart et al. |
| 6,516,217 | B1 | 2/2003 | Tsujita |
| 6,522,913 | B2 | 2/2003 | Swanson et al. |
| 6,542,767 | B1 | 4/2003 | McNichols et al. |
| 6,572,609 | B1 | 6/2003 | Farr et al. |
| 6,584,360 | B2 | 6/2003 | Francischelli et al. |
| 6,626,900 | B1 | 9/2003 | Sinofsky et al. |
| 6,648,883 | B2 | 11/2003 | Francischelli et al. |
| 6,658,279 | B2 | 12/2003 | Swanson et al. |
| 6,663,622 | B1 | 12/2003 | Foley et al. |
| 6,663,627 | B2 | 12/2003 | Francischelli et al. |
| 6,671,535 | B1 | 12/2003 | McNichols et al. |
| 6,697,657 | B1 | 2/2004 | Shehada et al. |
| 6,706,038 | B2 | 3/2004 | Francischelli et al. |
| 6,716,196 | B2 | 4/2004 | Lesh et al. |
| 6,743,225 | B2 | 6/2004 | Sanchez et al. |
| 6,746,401 | B2 | 6/2004 | Panescu |
| 6,761,716 | B2 | 7/2004 | Kadhiresan et al. |
| 6,825,928 | B2 | 11/2004 | Liu et al. |
| 6,936,047 | B2 | 8/2005 | Nasab et al. |
| 6,937,885 | B1 | 8/2005 | Lewis et al. |
| 6,942,657 | B2 | 9/2005 | Sinofsky et al. |
| 6,953,457 | B2 | 10/2005 | Farr et al. |
| 6,974,454 | B2 | 12/2005 | Hooven |
| 6,975,898 | B2 | 12/2005 | Seibel |
| 6,975,899 | B2 | 12/2005 | Faupel et al. |
| 6,979,290 | B2 | 12/2005 | Mourlas et al. |
| 6,989,010 | B2 | 1/2006 | Francischelli et al. |
| 7,001,383 | B2 | 2/2006 | Keidar |
| 7,029,470 | B2 | 4/2006 | Francischelli et al. |
| 7,047,068 | B2 | 5/2006 | Haissaguerre |
| 7,130,672 | B2 | 10/2006 | Pewzner et al. |
| 7,192,427 | B2 | 3/2007 | Chapelon et al. |
| 7,207,984 | B2 | 4/2007 | Farr et al. |
| 7,232,437 | B2 | 6/2007 | Berman et al. |
| 7,235,045 | B2 | 6/2007 | Wang et al. |
| 7,250,048 | B2 | 7/2007 | Francischelli et al. |
| 7,252,664 | B2 | 8/2007 | Nasab et al. |
| 7,255,695 | B2 | 8/2007 | Falwell et al. |
| 7,289,205 | B2 | 10/2007 | Yaroslavsky et al. |
| 7,306,593 | B2 | 12/2007 | Keidar et al. |
| 7,338,485 | B2 | 3/2008 | Brucker et al. |
| 7,357,796 | B2 | 4/2008 | Farr et al. |
| 7,367,944 | B2 | 5/2008 | Rosemberg et al. |
| 7,367,972 | B2 | 5/2008 | Francischelli et al. |
| 7,417,740 | B2 | 8/2008 | Alphonse et al. |
| 7,497,858 | B2 | 3/2009 | Chapelon et al. |
| 7,527,625 | B2 | 5/2009 | Knight et al. |
| 7,534,204 | B2 | 5/2009 | Starksen et al. |
| 7,539,530 | B2 | 5/2009 | Caplan et al. |
| 7,587,236 | B2 | 9/2009 | Demos et al. |
| 7,591,816 | B2 | 9/2009 | Wang et al. |
| 7,596,404 | B2 | 9/2009 | Maier et al. |
| 7,598,088 | B2 | 10/2009 | Balas |
| 7,640,046 | B2 | 12/2009 | Pastore |
| 7,662,152 | B2 | 2/2010 | Sharareh et al. |
| 7,681,579 | B2 | 3/2010 | Schwartz |
| 7,727,229 | B2 | 6/2010 | He et al. |
| 7,727,231 | B2 | 6/2010 | Swanson |
| 7,729,750 | B2 | 6/2010 | Tromberg et al. |
| 7,766,907 | B2 | 8/2010 | Dando et al. |
| 7,776,033 | B2 | 8/2010 | Swanson |
| 7,822,460 | B2 | 10/2010 | Halperin et al. |
| 7,824,397 | B2 | 11/2010 | McAuley |
| 7,824,399 | B2 | 11/2010 | Francischelli et al. |
| 7,837,676 | B2 | 11/2010 | Sinelnikov et al. |
| 7,846,157 | B2 | 12/2010 | Kozel |
| 7,862,561 | B2 | 1/2011 | Swanson et al. |
| 7,877,128 | B2 | 1/2011 | Schwartz |
| 7,918,850 | B2 | 4/2011 | Govari et al. |
| 7,930,016 | B1 | 4/2011 | Saadat |
| 7,942,871 | B2 | 5/2011 | Thapliyal et al. |
| 7,950,397 | B2 | 5/2011 | Thapliyal et al. |
| 7,974,683 | B2 | 7/2011 | Balaset et al. |
| 7,976,537 | B2 | 7/2011 | Lieber et al. |
| 7,979,107 | B2 | 7/2011 | Lin et al. |
| 7,992,573 | B2 | 8/2011 | Wilson et al. |
| 7,996,078 | B2 | 8/2011 | Paul et al. |
| 8,007,433 | B2 | 8/2011 | Iketani |
| 8,024,027 | B2 | 9/2011 | Freeman et al. |
| 8,025,661 | B2 | 9/2011 | Arnold et al. |
| 8,050,746 | B2 | 11/2011 | Saadat et al. |
| 8,078,266 | B2 | 12/2011 | Saadat et al. |
| 8,123,742 | B2 | 2/2012 | Berger |
| 8,123,745 | B2 | 2/2012 | Beeckler et al. |
| 8,129,105 | B2 | 3/2012 | Zuckerman |
| 8,131,350 | B2 | 3/2012 | Saadat et al. |
| 8,137,333 | B2 | 3/2012 | Saadat et al. |
| 8,144,966 | B2 | 3/2012 | Provenzano et al. |
| 8,146,603 | B2 | 4/2012 | Thapliyal et al. |
| 8,147,484 | B2 | 4/2012 | Lieber et al. |
| 8,152,795 | B2 | 4/2012 | Farr et al. |
| 8,160,680 | B2 | 4/2012 | Boyden et al. |
| 8,175,688 | B2 | 5/2012 | Lewis et al. |
| 8,180,436 | B2 | 5/2012 | Boyden et al. |

(56) References Cited

U.S. PATENT DOCUMENTS

| | | | |
|---|---|---|---|
| 8,188,446 | B2 | 5/2012 | Ohno |
| 8,195,271 | B2 | 6/2012 | Rahn |
| 8,203,709 | B2 | 6/2012 | Ishii |
| 8,219,183 | B2 | 7/2012 | Mashke et al. |
| 8,221,310 | B2 | 7/2012 | Saadat et al. |
| 8,235,985 | B2 | 8/2012 | Saadat et al. |
| 8,241,272 | B2 | 8/2012 | Arnold et al. |
| 8,267,926 | B2 | 9/2012 | Paul et al. |
| 8,277,444 | B2 | 10/2012 | Arnold et al. |
| 8,298,227 | B2 | 10/2012 | Leo et al. |
| 8,309,346 | B2 | 11/2012 | Zuckerman |
| 8,317,783 | B2 | 11/2012 | Cao et al. |
| 8,333,012 | B2 | 12/2012 | Rothe et al. |
| 8,353,907 | B2 | 1/2013 | Winkler et al. |
| 8,357,149 | B2 | 1/2013 | Govari et al. |
| 8,366,705 | B2 | 2/2013 | Arnold et al. |
| 8,369,922 | B2 | 2/2013 | Paul et al. |
| 8,374,682 | B2 | 2/2013 | Freeman et al. |
| 8,382,750 | B2 | 2/2013 | Brannan |
| 8,403,925 | B2 | 3/2013 | Miller et al. |
| 8,414,508 | B2 | 4/2013 | Thapliyal et al. |
| 8,417,321 | B2 | 4/2013 | Saadat et al. |
| 8,417,323 | B2 | 4/2013 | Uzunbajakava et al. |
| 8,419,613 | B2 | 4/2013 | Saadat et al. |
| 8,435,232 | B2 | 5/2013 | Aeby et al. |
| 8,444,639 | B2 | 5/2013 | Arnold et al. |
| 8,460,285 | B2 | 6/2013 | Wang et al. |
| 8,463,366 | B2 | 6/2013 | Freeman et al. |
| 8,500,730 | B2 | 8/2013 | Lee et al. |
| 8,504,132 | B2 | 8/2013 | Friedman et al. |
| 8,511,317 | B2 | 8/2013 | Thapliyal et al. |
| 8,540,704 | B2 | 9/2013 | Melsky et al. |
| 8,548,567 | B2 | 10/2013 | Maschke et al. |
| 8,556,892 | B2 | 10/2013 | Hong et al. |
| 8,583,220 | B2 | 11/2013 | Schwartz |
| 8,603,084 | B2 | 12/2013 | Fish et al. |
| 8,607,800 | B2 | 12/2013 | Thapliyal et al. |
| 8,628,520 | B2 | 1/2014 | Sharareh et al. |
| 8,641,705 | B2 | 2/2014 | Leo et al. |
| 8,641,706 | B2 | 2/2014 | Lieber et al. |
| 8,690,758 | B2 | 4/2014 | Matsumoto |
| 8,694,069 | B1 | 4/2014 | Kosa et al. |
| 8,702,690 | B2 | 4/2014 | Paul et al. |
| 8,709,008 | B2 | 4/2014 | Willis et al. |
| 8,728,077 | B2 | 5/2014 | Paul et al. |
| 8,755,860 | B2 | 6/2014 | Paul et al. |
| 8,774,906 | B2 | 7/2014 | Harks et al. |
| 8,808,281 | B2 | 8/2014 | Emmons et al. |
| 8,849,380 | B2 | 9/2014 | Patwardhan |
| 8,858,495 | B2 | 10/2014 | Tegg et al. |
| 8,876,817 | B2 | 11/2014 | Avitall et al. |
| 8,882,697 | B2 | 11/2014 | Celermajer et al. |
| 8,894,589 | B2 | 11/2014 | Leo et al. |
| 8,894,641 | B2 | 11/2014 | Brannan |
| 8,900,219 | B2 | 12/2014 | Sinofsky et al. |
| 8,900,225 | B2 | 12/2014 | Bar-Tal et al. |
| 8,900,228 | B2 | 12/2014 | Grunewald et al. |
| 8,900,229 | B2 | 12/2014 | Govari et al. |
| 8,906,011 | B2 | 12/2014 | Gelbart et al. |
| 8,915,878 | B2 | 12/2014 | Winkler et al. |
| 8,923,959 | B2 | 12/2014 | Boveja et al. |
| 8,926,604 | B2 | 1/2015 | Govari et al. |
| 8,929,973 | B1 | 1/2015 | Webb et al. |
| 8,948,851 | B2 | 2/2015 | Leblond et al. |
| 8,951,247 | B2 | 2/2015 | Ding et al. |
| 8,986,292 | B2 | 3/2015 | Sliwa et al. |
| 8,986,298 | B2 | 3/2015 | Lee et al. |
| 8,998,890 | B2 | 4/2015 | Paul et al. |
| 8,998,892 | B2 | 4/2015 | Winkler et al. |
| 8,998,893 | B2 | 4/2015 | Avitall |
| 9,008,746 | B2 | 4/2015 | Pastore et al. |
| 9,014,789 | B2 | 4/2015 | Mercader et al. |
| 9,084,611 | B2 | 7/2015 | Amirana et al. |
| 9,087,368 | B2 | 7/2015 | Tearney et al. |
| 9,186,066 | B2 | 11/2015 | Tearney et al. |
| 9,220,411 | B2 | 12/2015 | Hillman |
| 9,233,241 | B2 | 1/2016 | Long |
| 9,277,865 | B2 | 3/2016 | Yamaguchi et al. |
| 10,076,238 | B2 | 9/2018 | Amirana et al. |
| 10,143,517 | B2 | 12/2018 | Ransbury et al. |
| 10,568,535 | B2 | 2/2020 | Roberts et al. |
| 10,682,179 | B2 | 6/2020 | Ransbury et al. |
| 10,716,462 | B2 | 7/2020 | Amirana et al. |
| 10,722,301 | B2 | 7/2020 | Amirana et al. |
| 10,736,512 | B2 * | 8/2020 | Mercader ........... A61B 1/00082 |
| 10,779,904 | B2 | 9/2020 | Ransbury et al. |
| 11,096,584 | B2 | 8/2021 | Mercader et al. |
| 11,457,817 | B2 | 10/2022 | Sarvazyan |
| 11,559,192 | B2 | 1/2023 | Amirana et al. |
| 11,559,352 | B2 | 1/2023 | Amirana et al. |
| 12,075,980 | B2 | 9/2024 | Amirana et al. |
| 12,076,081 | B2 | 9/2024 | Amirana et al. |
| 12,295,795 | B2 | 5/2025 | Ransbury et al. |
| 12,343,114 | B2 | 7/2025 | Mercader et al. |
| 12,539,043 | B2 | 2/2026 | Sarvazyan |
| 2002/0042556 | A1 | 4/2002 | Sugimoto et al. |
| 2002/0123666 | A1 | 9/2002 | Matsumoto |
| 2002/0143326 | A1 | 10/2002 | Foley et al. |
| 2003/0028188 | A1 | 2/2003 | Paddock et al. |
| 2003/0120142 | A1 | 6/2003 | Dubuc et al. |
| 2003/0120144 | A1 | 6/2003 | Grabek et al. |
| 2003/0125719 | A1 | 7/2003 | Furnish |
| 2003/0208252 | A1 | 11/2003 | O'Boyle et al. |
| 2004/0073206 | A1 | 4/2004 | Foley et al. |
| 2004/0092806 | A1 | 5/2004 | Sagon et al. |
| 2004/0097788 | A1 | 5/2004 | Mourlas et al. |
| 2004/0138656 | A1 | 7/2004 | Francischelli et al. |
| 2004/0187875 | A1 | 9/2004 | He et al. |
| 2004/0215310 | A1 | 10/2004 | Amirana |
| 2004/0267326 | A1 | 12/2004 | Ocel et al. |
| 2005/0014995 | A1 | 1/2005 | Amundson et al. |
| 2005/0043637 | A1 | 2/2005 | Caplan et al. |
| 2005/0070987 | A1 | 3/2005 | Erickson |
| 2005/0075629 | A1 | 4/2005 | Chapelon et al. |
| 2005/0119523 | A1 | 6/2005 | Starksen et al. |
| 2005/0119548 | A1 | 6/2005 | Lin et al. |
| 2005/0197530 | A1 | 9/2005 | Wallace et al. |
| 2005/0197623 | A1 | 9/2005 | Leeflang et al. |
| 2005/0215899 | A1 | 9/2005 | Trahey et al. |
| 2005/0228452 | A1 | 10/2005 | Mourlas et al. |
| 2005/0251125 | A1 | 11/2005 | Pless et al. |
| 2005/0283195 | A1 | 12/2005 | Pastore et al. |
| 2006/0009756 | A1 | 1/2006 | Francischelli et al. |
| 2006/0013454 | A1 | 1/2006 | Flewelling et al. |
| 2006/0025760 | A1 | 2/2006 | Podhajsky |
| 2006/0089636 | A1 | 4/2006 | Christopherson et al. |
| 2006/0122583 | A1 | 6/2006 | Pesach et al. |
| 2006/0122587 | A1 | 6/2006 | Sharareh |
| 2006/0184048 | A1 | 8/2006 | Saadat |
| 2006/0229515 | A1 | 10/2006 | Sharareh et al. |
| 2006/0229594 | A1 | 10/2006 | Francischelli et al. |
| 2006/0278246 | A1 | 12/2006 | Eng et al. |
| 2007/0015964 | A1 | 1/2007 | Eversull et al. |
| 2007/0016079 | A1 | 1/2007 | Freeman et al. |
| 2007/0016130 | A1 | 1/2007 | Leeflang et al. |
| 2007/0038126 | A1 | 2/2007 | Pyle et al. |
| 2007/0049827 | A1 | 3/2007 | Donaldson et al. |
| 2007/0083217 | A1 | 4/2007 | Eversull et al. |
| 2007/0167828 | A1 | 7/2007 | Saadat |
| 2007/0179487 | A1 | 8/2007 | Tearney et al. |
| 2007/0185479 | A1 | 8/2007 | Lau |
| 2007/0225697 | A1 | 9/2007 | Shroff et al. |
| 2007/0270717 | A1 | 11/2007 | Tang et al. |
| 2007/0270789 | A1 | 11/2007 | Berger |
| 2007/0270792 | A1 | 11/2007 | Hennemann et al. |
| 2007/0270795 | A1 | 11/2007 | Francischelli et al. |
| 2007/0276259 | A1 | 11/2007 | Okawa et al. |
| 2007/0287886 | A1 | 12/2007 | Saadat |
| 2007/0293724 | A1 | 12/2007 | Saadat et al. |
| 2008/0009747 | A1 | 1/2008 | Saadat et al. |
| 2008/0015569 | A1 | 1/2008 | Saadat et al. |
| 2008/0021275 | A1 | 1/2008 | Tearney et al. |
| 2008/0033241 | A1 | 2/2008 | Peh et al. |
| 2008/0058650 | A1 | 3/2008 | Saadat et al. |

(56) References Cited

U.S. PATENT DOCUMENTS

2008/0058785 A1 3/2008 Boyden et al.
2008/0058786 A1 3/2008 Boyden et al.
2008/0097476 A1 4/2008 Peh et al.
2008/0101677 A1 5/2008 Mashke et al.
2008/0103355 A1 5/2008 Boyden et al.
2008/0119694 A1* 5/2008 Lee .......................... A61B 5/01 600/127
2008/0125634 A1 5/2008 Ryan et al.
2008/0154257 A1 6/2008 Sharareh et al.
2008/0172049 A1 7/2008 Bredno et al.
2008/0183036 A1 7/2008 Saadat et al.
2008/0212867 A1 9/2008 Provenzano et al.
2008/0214889 A1 9/2008 Saadat et al.
2008/0221448 A1 9/2008 Khuri-Yakub et al.
2008/0228032 A1 9/2008 Starksen et al.
2008/0228079 A1 9/2008 Donaldson et al.
2008/0243214 A1 10/2008 Koblish
2008/0275300 A1 11/2008 Rothe et al.
2008/0281293 A1 11/2008 Peh et al.
2008/0300589 A1 12/2008 Paul et al.
2009/0012367 A1 1/2009 Chin et al.
2009/0030276 A1 1/2009 Saadat et al.
2009/0030412 A1 1/2009 Willis et al.
2009/0054803 A1 2/2009 Saadat et al.
2009/0062790 A1 3/2009 Malchano et al.
2009/0076373 A1 3/2009 Maschke
2009/0076375 A1 3/2009 Maschke
2009/0082623 A1 3/2009 Rothe et al.
2009/0082660 A1 3/2009 Rahn et al.
2009/0125022 A1 5/2009 Saadat et al.
2009/0131931 A1 5/2009 Lee et al.
2009/0143640 A1 6/2009 Saadat et al.
2009/0203962 A1 8/2009 Miller et al.
2009/0204069 A1 8/2009 Hirszowicz et al.
2009/0221871 A1 9/2009 Peh et al.
2009/0227999 A1 9/2009 Willis et al.
2009/0253991 A1 10/2009 Balas et al.
2009/0275799 A1 11/2009 Saadat et al.
2009/0281541 A1 11/2009 Ibrahim et al.
2009/0292211 A1 11/2009 Lin et al.
2009/0299354 A1 12/2009 Melsky et al.
2009/0299363 A1 12/2009 Saadat et al.
2009/0306643 A1 12/2009 Pappone et al.
2009/0326385 A1 12/2009 Hendriks et al.
2010/0022832 A1 1/2010 Makiyama
2010/0041986 A1 2/2010 Nguyen et al.
2010/0056966 A1 3/2010 Toth
2010/0081127 A1 4/2010 Maier et al.
2010/0081873 A1 4/2010 Tanimura et al.
2010/0081948 A1 4/2010 Pastore et al.
2010/0084563 A1 4/2010 Ohno
2010/0114094 A1 5/2010 Thapliyal et al.
2010/0125165 A1 5/2010 Torii et al.
2010/0130836 A1 5/2010 Malchano et al.
2010/0152728 A1 6/2010 Park et al.
2010/0198065 A1 8/2010 Thapliyal et al.
2010/0204544 A1 8/2010 Takei
2010/0204561 A1 8/2010 Saadat
2010/0228247 A1 9/2010 Paul et al.
2010/0241117 A1 9/2010 Paul et al.
2010/0274364 A1 10/2010 Pacanowsky
2010/0312094 A1 12/2010 Guttman et al.
2010/0312096 A1 12/2010 Guttman et al.
2010/0331838 A1 12/2010 Ibrahim et al.
2011/0009793 A1 1/2011 Lucero
2011/0019893 A1 1/2011 Rahn et al.
2011/0029058 A1 2/2011 Swanson
2011/0042580 A1 2/2011 Wilson et al.
2011/0066147 A1 3/2011 He et al.
2011/0071647 A1 3/2011 Mahon
2011/0082450 A1 4/2011 Melsky et al.
2011/0082451 A1 4/2011 Melsky et al.
2011/0082452 A1 4/2011 Melsky et al.
2011/0117025 A1 5/2011 Dacosta et al.
2011/0144524 A1 6/2011 Fish et al.
2011/0224494 A1 9/2011 Piskun et al.
2011/0230903 A1 9/2011 Bertolero
2011/0275932 A1 11/2011 Leblond et al.
2011/0276046 A1 11/2011 Heimbecher et al.
2011/0282250 A1 11/2011 Fung et al.
2011/0313417 A1 12/2011 De La Rama et al.
2012/0023638 A1 2/2012 Leicester
2012/0029504 A1 2/2012 Afonso et al.
2012/0109031 A1 5/2012 Vollbrecht
2012/0123276 A1 5/2012 Govari et al.
2012/0143177 A1 6/2012 Avitall
2012/0150046 A1 6/2012 Watson et al.
2012/0184812 A1 7/2012 Terakawa
2012/0184813 A1 7/2012 Terakawa
2012/0197243 A1 8/2012 Sherman et al.
2012/0215112 A1 8/2012 Lewis et al.
2012/0220999 A1 8/2012 Long
2012/0259263 A1 10/2012 Celermajer et al.
2012/0323237 A1 12/2012 Paul et al.
2012/0326055 A1 12/2012 Wilson et al.
2013/0006116 A1 1/2013 Kim et al.
2013/0023865 A1 1/2013 Steinke et al.
2013/0030425 A1 1/2013 Stewart et al.
2013/0079645 A1 3/2013 Amirana et al.
2013/0085416 A1 4/2013 Mest
2013/0096593 A1 4/2013 Thapliyal et al.
2013/0096594 A1 4/2013 Thapliyal et al.
2013/0102862 A1 4/2013 Amirana et al.
2013/0107002 A1 5/2013 Kikuchi
2013/0137949 A1 5/2013 Freeman et al.
2013/0150693 A1 6/2013 D'Angelo et al.
2013/0150732 A1 6/2013 Manzke et al.
2013/0158545 A1 6/2013 Govari et al.
2013/0172742 A1 7/2013 Rankin et al.
2013/0172875 A1 7/2013 Govari et al.
2013/0226163 A1 8/2013 Peled et al.
2013/0237841 A1 9/2013 Freeman et al.
2013/0253330 A1 9/2013 Demos
2013/0261455 A1 10/2013 Thapliyal et al.
2013/0267875 A1 10/2013 Thapliyal et al.
2013/0281920 A1 10/2013 Hawkins et al.
2013/0282005 A1 10/2013 Koch et al.
2013/0289358 A1 10/2013 Melsky et al.
2013/0289672 A1 10/2013 Hakomori et al.
2013/0296840 A1 11/2013 Condie et al.
2013/0310680 A1 11/2013 Werahera et al.
2013/0331831 A1 12/2013 Werneth et al.
2014/0031802 A1 1/2014 Melsky
2014/0058203 A1 2/2014 Naito
2014/0058244 A1 2/2014 Krocak
2014/0058246 A1 2/2014 Boveja et al.
2014/0081253 A1 3/2014 Kumar et al.
2014/0088418 A1 3/2014 Radulescu et al.
2014/0107430 A1 4/2014 Deno et al.
2014/0121537 A1 5/2014 Aeby et al.
2014/0121660 A1 5/2014 Hauck
2014/0148703 A1 5/2014 Deladi et al.
2014/0163360 A1 6/2014 Stevens-Wright et al.
2014/0163543 A1 6/2014 Allison et al.
2014/0171806 A1 6/2014 Govari et al.
2014/0171936 A1 6/2014 Govari et al.
2014/0180273 A1 6/2014 Nair
2014/0194867 A1 7/2014 Fish et al.
2014/0194869 A1 7/2014 Leo et al.
2014/0243843 A1 8/2014 Havel et al.
2014/0275972 A1 9/2014 George et al.
2014/0276687 A1 9/2014 Goodman et al.
2014/0276771 A1 9/2014 Miller et al.
2014/0316280 A1 10/2014 Mueller et al.
2014/0324085 A1 10/2014 Thapliyal et al.
2014/0350547 A1 11/2014 Sharareh et al.
2014/0357956 A1 12/2014 Salahieh et al.
2014/0378843 A1 12/2014 Valdes et al.
2014/0378846 A1 12/2014 Hosoda et al.
2015/0038824 A1 2/2015 Lupotti
2015/0073245 A1 3/2015 Klimovitch et al.
2015/0099979 A1 4/2015 Caves et al.
2015/0141847 A1 5/2015 Sarvazyan et al.
2015/0148630 A1 5/2015 Meester

(56) References Cited

U.S. PATENT DOCUMENTS

| | | | | |
|---|---|---|---|---|
| 2015/0164332 | A1 | 6/2015 | Mercader et al. | |
| 2015/0182279 | A1 | 7/2015 | Ashton et al. | |
| 2015/0196202 | A1 | 7/2015 | Mercader et al. | |
| 2015/0216398 | A1 | 8/2015 | Yang et al. | |
| 2015/0327753 | A1 | 11/2015 | Amirana et al. | |
| 2015/0346100 | A1 | 12/2015 | Racowsky et al. | |
| 2015/0374217 | A1* | 12/2015 | Sinofsky | A61B 1/07 600/104 |
| 2016/0051321 | A1 | 2/2016 | Salahieh et al. | |
| 2016/0120599 | A1 | 5/2016 | Amirana et al. | |
| 2016/0120602 | A1 | 5/2016 | Ransbury et al. | |
| 2016/0143522 | A1 | 5/2016 | Ransbury et al. | |
| 2016/0228206 | A1 | 8/2016 | Bell et al. | |
| 2017/0014202 | A1* | 1/2017 | Ransbury | A61B 18/06 |
| 2017/0020394 | A1 | 1/2017 | Harrington | |
| 2017/0035341 | A1 | 2/2017 | Nagale et al. | |
| 2017/0071664 | A1 | 3/2017 | Lim et al. | |
| 2017/0135559 | A1 | 5/2017 | Horrisberger et al. | |
| 2017/0164999 | A1 | 6/2017 | Hettel | |
| 2018/0263476 | A1 | 9/2018 | Amirana et al. | |
| 2019/0053849 | A1 | 2/2019 | Ransbury et al. | |
| 2019/0110838 | A1 | 4/2019 | Martinez et al. | |
| 2019/0254735 | A1 | 8/2019 | Stewart et al. | |
| 2019/0262056 | A1 | 8/2019 | Yang et al. | |
| 2019/0350647 | A1 | 11/2019 | Ramberg et al. | |
| 2020/0008681 | A1 | 1/2020 | Sarvazyan | |
| 2020/0330727 | A1 | 10/2020 | Creighton | |
| 2020/0352425 | A1 | 11/2020 | Amirana et al. | |
| 2020/0352644 | A1 | 11/2020 | Ransbury et al. | |
| 2020/0352645 | A1 | 11/2020 | Amirana et al. | |
| 2021/0045834 | A1 | 2/2021 | Amirana et al. | |
| 2021/0205017 | A1 | 7/2021 | Amirana et al. | |
| 2021/0369118 | A1 | 12/2021 | Sarvazyan | |
| 2022/0047150 | A1 | 2/2022 | Wang et al. | |
| 2022/0133172 | A1 | 5/2022 | Ransbury et al. | |
| 2022/0142482 | A1 | 5/2022 | Mercader et al. | |
| 2022/0226665 | A1* | 7/2022 | Uto | A61B 1/07 |
| 2023/0293000 | A1 | 9/2023 | Amirana et al. | |
| 2023/0404373 | A1 | 12/2023 | Ransbury et al. | |
| 2025/0127386 | A1 | 4/2025 | Amirana et al. | |

FOREIGN PATENT DOCUMENTS

| | | | |
|---|---|---|---|
| CN | 101199410 | | 6/2008 |
| CN | 102099671 | | 6/2011 |
| CN | 102397104 | | 4/2012 |
| CN | 203525125 | | 4/2014 |
| CN | 106028914 | | 10/2016 |
| DE | 102005021205 | | 11/2006 |
| DE | 102011083522 | | 3/2013 |
| EP | 2691041 | | 2/2014 |
| EP | 2 889 013 | | 7/2015 |
| JP | 60182928 | | 9/1985 |
| JP | 63-262613 | | 10/1988 |
| JP | 10150177 | | 6/1998 |
| JP | 2006158546 | | 6/2006 |
| JP | 20090148550 | A | 7/2009 |
| JP | 2011/212423 | | 10/2011 |
| JP | 201252882 | A | 3/2012 |
| JP | 20130544551 | A | 12/2013 |
| JP | 20150128586 | A | 7/2015 |
| JP | 2018158114 | A | 10/2018 |
| NL | 2002010 | | 10/2009 |
| WO | WO 1997/037622 | | 10/1997 |
| WO | WO 1999/013934 | | 3/1999 |
| WO | WO 2001/001854 | | 1/2001 |
| WO | WO 2001/072214 | | 10/2001 |
| WO | WO 2003/092520 | | 11/2003 |
| WO | WO 2004/028353 | | 4/2004 |
| WO | WO 2006/028824 | | 3/2006 |
| WO | 2006108143 | A2 | 10/2006 |
| WO | 2007041542 | A2 | 4/2007 |
| WO | WO 2007/109554 | | 9/2007 |
| WO | WO 2007/127228 | | 11/2007 |
| WO | WO 2008/028149 | | 3/2008 |
| WO | 2008054423 | A1 | 5/2008 |
| WO | WO 2008/114748 | | 9/2008 |
| WO | WO 2008/154578 | | 12/2008 |
| WO | WO 2010/075450 | | 7/2010 |
| WO | WO 2011/025640 | | 3/2011 |
| WO | WO 2011/113162 | | 9/2011 |
| WO | WO 2012038824 | | 3/2012 |
| WO | WO 2012/049621 | | 4/2012 |
| WO | WO 2012/067682 | | 5/2012 |
| WO | 20120131577 | A2 | 10/2012 |
| WO | WO 2013/044182 | | 3/2013 |
| WO | WO 2013/068885 | | 5/2013 |
| WO | WO 2013/116316 | | 8/2013 |
| WO | WO 2013/169340 | | 11/2013 |
| WO | WO 2014/028770 | | 2/2014 |
| WO | 2014205256 | A2 | 12/2014 |
| WO | WO 2015/073871 | | 5/2015 |
| WO | WO 2015/077474 | | 5/2015 |
| WO | WO 2016/073476 | | 5/2016 |
| WO | WO 2016/073492 | | 5/2016 |
| WO | WO 2016/086160 | | 6/2016 |
| WO | WO 2017/015257 | | 1/2017 |

OTHER PUBLICATIONS

Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.

Asfour et al, "Signal decomposition of transmembrane voltage-sensitive dye fluorescence using a multiresolution wavelet analysis" IEEE Trans Biomed Eng. 2011; 58: 2083-2093.

Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.

Boersma et al,. "Pulmonary vein isolation by duty-cycled bipolar and unipolar radiofrequency energy with a multielectrode ablation catheter". Heart Rhythm5:1635-1642, 2008.

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).

Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).

Buch et al. "Epicardial catheter ablation of atrial fibrillation." Minerva Med. 2009; 100: 151-157.

Cancio et al., "Hyperspectral Imaging: A New Approach to the Diagnosis of Hemorrhagic Shock", The Journal of Trauma, 2006, vol. 60, No. 5: 1087-1095.

Chance et al, "Fluorescence measurements of mitochondrial pyridine nucleotide in aerobiosis and anaerobiosis" Nature. 1959; 184: 931-4.

Coremans et al, "Pretransplantation assessment of renal viability with NADH fluorimetry", Kidney International, vol. 57, (2000), pp. 671-683.

D'Avila A. "Epicardial catheter ablation of ventricular tachycardia." Heart Rhythm. 2008; 5: S73-5.

Demos et al, "Real time assessment of RF cardiac tissue ablation with optical spectroscopy", Opt Express. 2008; 16: 15286-15296.

Dickfeld et al, "Characterization of Radiofrequency Ablation Lesions With Gadolinium-Enhanced Cardiovascular Magnetic Resonance Imaging" J Am Coll Cardiol. 2006; 47: 370-378.

Dukkipati et al, "Visual balloon-guided point-by-point ablation: reliable, reproducible, and persistent pulmonary vein isolation", Circ Arrhythm Electrophysiol. 2010; 3: 266-273.

Dumas et al, "Myocardial electrical impedance as a predictor of the quality of RF-induced linear lesions." Physiol Meas. 2008; 29: 1195-1207.

(56) References Cited

OTHER PUBLICATIONS

Dyer, B., et al., Heart, "The Application of Autofluorescence Lifetime Metrology as a Novel Label-free Technique for the Assessment of Cardiac Disease", vol. 11, Issue Supplement 3, p. 186, Jun. 2014.
Fleming et al, "Real-time monitoring of cardiac redio-frequency ablation lesion formation using an optical coherence tomography forward-imaging catheter", Journal of Biomedical Optics, May/Jun. 2010, vol. 15(3).
Fleming et al, "Toward guidance of epicardial cardiac radiofrequency ablation therapy using optical coherence tomography" J Biomed Opt. 2010; 15: 041510.
Girard et al, "Contrast-enhanced C-arm CT evaluation of radiofrequency ablation lesions in the left ventricle", JACC Cardiovasc Imaging. 2011; 4: 259-268.
Grimard et al., "Percutaneous epicardial radiofrequency ablation of ventricular arrhythmias after failure of endocardial approach: a 9-year experience" J Cardiovasc Electrophysiol. 2010; 21: 56-61.
Henz et al, "Simultaneous epicardial and endocardial substrate mapping and radiofrequency catheter ablation as first-line treatment for ventricular tachycardia and frequent ICD shocks in chronic chagasic cardiomyopathy" J Interv Card Electrophysiol. 2009; 26: 195-205.
Himel et al, "Translesion stimulus-excitation delay indicates quality of linear lesions produced by radiofrequency ablation in rabbit hearts", Physiol Meas. 2007; 28: 611-623.
Kalman, J.M., et al., "Cardiac Magnetic Resonance Imaging to Detect Non-Contiguous Scar Following Atrial Fibrillation Ablation: Identifying our Knowledge Gaps", European Heart Journal, Editorial, pp. 1-3, Feb. 26, 2014.
Kay et al, "Locations of ectopic beats coincide with spatial gradients of NADH in a regional model of low-flow reperfusion", Am J Physiol Heart Circ Physiol. 2008; 294: H2400-5.
Khoury et al., "Localizing and Quantifying Ablation Lesions in the Left Ventricle by Myocardial Contrast Echocardiography", J Cardiovasc Electrophysiol. 2004; 15: 1078-1087.
Kim et al, "Materials for multifunctional balloon catheters with capabilities in cardiac electrophysiological mapping and ablation therapy", Nat Mater. 2011; 10: 316-323.
Kistler, P.M., et al., "The Impact of CT Image Integration into an Electroanatomic Mapping System on Clinical Outcomes of Catheter Ablation of Atrial Fibrillation", Journal of Cardiovascular Electyrophysiology, vol. 17, Issue 10, pp. 1093-1101, Oct. 2006.
Lardo, et al "Visualization and temporal/spatial characterization of cardiac radiofrequency ablation lesions using magnetic resonance imaging", Circulation. 2000; 102: 698-705.
Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.
Lo et al, "Three-dimensional electroanatomic mapping systems in catheter ablation of atrial fibrillation", Circ J. 2010; 74: 18-23.
Malchano, Z.J., "Integration of Cardiac CT/MR Imaging with Three-Dimensional Electroanatomical Mapping to Guide Catheter Manipulation in the Left Atrium: Implications for Catheter Ablation of Atrial Fibrillation", Journal of Cardiovascular Electrophysiology, vol. 17, Issue 11, pp. 1221-1229, Nov. 2006.
Mayevsky et al. "Oxidation-reduction states of NADH in vivo: from animals to clinical use", Mitochondrion. 2007; 7: 330-339.
Melby et al, "Atrial fibrillation propagates through gaps in ablation lines: implications for ablative treatment of atrial fibrillation", Heart Rhythm. 2008; 5: 1296-1301.
Menes et al, "Laparoscopy: searching for the proper insufflation gas" Surg Endosc. 2000; 14: 1050-1056.
Meng et al "A comparative study of fibroid ablation rates using radio frequency or high-intensity focused ultrasound", Cardiovasc Intervent Radiol. 2010; 33: 794-799.
Mercader et al, "NADH as an Endogenous Marker of Cardiac Tissue Injury at the Site of Radiofrequency Ablation", The George Washington University, Washington DC, Mar. 18, 2011.
Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.
Naito, H., et al., "Use of Nadh Fluorescence Imaging for Early Detection of Energy Failure and a Prediction of Infarction", Critical Care Medicine, vol. 39, Issue 12, pp. 40, Dec. 2011.
Nath et al, "Basic aspects of radiofrequency catheter ablation", J Cardiovasc Electrophysiol. 1994; 5: 863-876.
Niu et al, "An acute experimental model demonstrating 2 different forms of sustained atrial tachyarrhythmias". Circ Arrhythm Electrophysiol. 2009; 2: 384-392.
Perez et al. "Effects of gap geometry on conduction through discontinuous radiofrequency lesions" Circulation. 2006; 113: 1723-1729.
Ranji et al, "Fluorescence spectroscopy and imaging of myocardial apoptosis", Journal of Biomedical Optics 11(6), 064036 (Nov./Dec. 2006).
Ranji et al, "Quantifying Acute Myocardial Injury Using Ratiometric Fluorometry", IEEE Trans Biomed Eng. May 2009; 56(5): 1556-1563.
Riess et al, "Altered NADH and improved function by anesthetic and ischemic preconditioning in guinea pig intact hearts", Am J Physiol Heart Circ Physiol 283; H53-H60, Mar. 14, 2002.
Robertson, J.O., "Quantification of the Functional Consequences of Atrial Fibrillation and Surgical Ablation on the Left Atrium Using Cardiac Magnetic Resonance Imaging", European Journal of Cardio-Thoracic Surgery, vol. 46, Issue 4, pp. 720-728, Oct. 1, 2014.
Roger et al, "American Heart Association Stastics Committee and Stroke Subcommittee. Heart disease and stroke statistics—2011 update; a report from American Heart Association", Circulation 2011; 123: e18-e209.
Sethuraman et al., "Spectroscopic Intravascular Photoacoustic Imaging to Differentiate Atherosclerotic Plaques", Optics Express, vol. 16, No. 5, pp. 3362-3367, Mar. 3, 2008.
Smith, S., et al., "Imaging Appearances Following Thermal Ablation", Clinical Radiology, vol. 63, Issue 1, pp. 1-11, Jan. 2008.
Sosa et al, "Epicardial mapping and ablation techniques to control ventricular tachycardia". J Cardiovasc Electrophysiol. 2005; 16: 449-452.
Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.
Swartling et al, "Changes in tissue optical properties due to radio-frequency ablation of myocardium", Med Biol Eng Comput. 2003; 41: 403-409.
Swift et al, "Controlled regional hypoperfusion in Langendorff heart preparations". Physiol Meas. 2008; 29: 269-79.
Swift, L.M., et al., "Properties of Blebbistatin for Cardiac Optical Mapping and Other Imaging Applications", European Journal of Physiology, vol. 464, Issue 5, pp. 503-512, Nov. 2012.
Swift, Luther Mitchell, "Real-Time Visualization of Cardiac Ablation Lesions Using Endogenous NADH Fluorescence and Reflected Light", A dissertation submitted to The Faculty of The Columbian College of Arts and Sciences of The George Washington University in partial fulfillment of the requirements for the degree of Doctor of Philosophy, Jul. 23, 2013.
Van Haesendonck C, Sinnaeve A, Willems R, Vandenbulcke F, Stroobandt R, . "Biophysical and electrical aspects of radiofrequency catheter ablation". Acta Cardiol 50: 105-115, 1995.
Vetterlein et al, "Extent of damage in aschemic, nonreperfused myocardium of anesthetized rats", Am J Physiol Heart Circ Physiol 285: H755-H765, 2003.
Vo-Dinh et al., "A Hyperspectral Imaging System for In Vivo Optical Diagnostics", IEEE Engineering in Medicine and Biology Magazine, pp. 40-49, Sep./Oct. 2004.
Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.

(56) References Cited

OTHER PUBLICATIONS

Wu, H., et al., "Real-Time Monitoring of Radiofrequency Ablation and Postablation Assessment: Accuracy of Contrast-Enhanced US in Experimental Rat Liver Model", Radiology, vol. 270, No. 1, pp. 107-116, Jan. 2014.
Yokoyama et al, "Novel contact force sensor incorporated in irrigated radiofrequency ablation catheter predicts lesion size and incidence of steam pop and thrombus", Circ Arrhythm Electrophysiol. 2008; 1: 354-362.
Zuzak et al., "Characterization of a Near-Infrared Laparoscopic Hyperspectral Imaging System for Minimally Invasive Surgery", Analytical Chemistry, vol. 79, No. 12, pp. 4709-4715, Jun. 15, 2007.
Swift et al., "Hyperspectral Imaging for Label-Free in Vivo Identification of Myocardial Scars and Sites of Radiofrequency Ablation Lesions," Heart Rhythm, vol. 15, No. 4, pp. 564-575, Apr. 2018.—in Notice of Allowance in of Oct. 31, 2025.

* cited by examiner

SYSTEMS AND METHODS FOR LESION FORMATION AND ASSESSMENT

RELATED APPLICATION

This application claims the benefit of and priority to U.S. Provisional Application Ser. No. 63/057,569, filed on Jul. 28, 2020, which is incorporated herein by reference in its entirety.

FIELD

The present disclosure generally relates to catheters, and more particularly ablation and visualization catheters.

BACKGROUND

Ablation therapy is a minimally invasive procedure that applies energy to tissue to cause cell death. For example, ablation therapy can be used to remove or destroy abnormal tissue types (for example, tumors). Another example is the use of ablation therapy to treat atrial fibrillation (AF). Most episodes in patients with AF are known to be triggered by focal electrical activity originating from within muscle sleeves that extend into the Pulmonary Veins (PV). Atrial fibrillation may also be triggered by focal activity within the superior vena cava or other atrial structures, i.e. other cardiac tissue within the heart's conduction system. These focal triggers can also cause atrial tachycardia that is driven by reentrant electrical activity (or rotors), which may then fragment into a multitude of electrical wavelets that are characteristic of atrial fibrillation. Furthermore, prolonged AF can cause functional alterations in cardiac cell membranes and these changes further perpetuate atrial fibrillation. Physicians use a catheter to direct energy to either destroy focal triggers or to form electrical isolation lines isolating the triggers from the heart's remaining conduction system.

One issue with ablation therapy is the lack of visual feedback that often results in ineffective or incomplete ablation, and recurrence of the underlying medical condition. Therefore, there is a need for system and method for forming and verifying proper lesions to improve outcomes and reduce costs.

SUMMARY

According to some aspects of the present disclosure, there is provided a catheter for visualizing ablated tissue that includes a catheter body and a distal tip positioned at a distal end of the catheter body. The distal tip has one or more ports for an exchange of light energy between the distal tip and tissue. A lumen can extend through the catheter body and the distal tip and has one more openings corresponding to the one or more ports on the distal tip. One or more optical fibers are configured to extend through the lumen and the one or more openings to an outer surface of the distal tip through one or more ports in the distal tip such that the one or more optical fibers direct the light energy to and from the tissue through the one or more ports.

In some embodiments, the catheter can also include one or more channels configured to connect the one or more openings in the lumen to the one or more ports of the distal tip to direct the one or more optical fibers to the outer surface of the distal tip.

In some embodiments, the one or more ports are disposed circumferentially along the distal tip and are spaced apart from one another by equal distance. In some embodiments, one of the one or more ports is disposed at a distal end of the distal tip to direct light to tissue in front of the distal tip. In some embodiments, the one or more fibers are fixedly coupled to the one or more ports in the distal tip. In some embodiments, the light for illuminating the tissue has at least one wavelength between about 300 nm and about 400 nm.

In some embodiments, the distal tip is configured to deliver ablation energy to the tissue. The ablation energy is selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

In some embodiments, the tissue is selected from a group consisting of skeletal muscle, liver, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, genitourinary, and kidney.

A system for visualizing ablated tissue is provided that includes a catheter comprising a catheter body and a distal tip positioned at a distal end of the catheter body with the distal tip having one or more ports for exchange of light energy between the distal tip and tissue. A lumen extends through the catheter body and the distal tip and has one more openings corresponding to the one or more ports on the distal tip. One or more optical fibers are configured to extend through the lumen and the one or more openings to an outer surface of the distal tip through one or more ports in the distal tip such that the one or more optical fibers direct the light energy to and from the tissue through the one or more ports. The system also includes a light source, a light measuring instrument, and one or more optical fibers in communication with the light source and the light measuring instrument and extending through the catheter body into the distal tip. The one or more optical fibers are configured to pass light energy from the light source to the light directing member for illuminating tissue outside the distal tip and the one or more optical fibers are configured to relay light energy reflected from the tissue to the light measuring instrument.

In some embodiments, the one or more ports are disposed circumferentially along the distal tip and are spaced apart from one another by equal distance. In some embodiments, the system can also include an ultrasound transducer. In some embodiments, the light for illuminating the tissue has at least one wavelength between about 300 nm and about 400 nm. In some embodiments, the light measuring instrument is configured to detect returned light having a wavelength between about 450 nm and 470 nm is monitored.

In some embodiments, the system can include a source of ablation energy in communication with the distal tip to deliver ablation energy to the tissue. The ablation energy is selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

According to some aspects of the present disclosure, there is provided a method for visualizing ablated tissue comprising advancing a catheter to a cardiac tissue in need of ablation. The catheter comprising a catheter body and a distal tip positioned at a distal end of the catheter body, with the distal tip having one or more ports for exchange of light energy between the distal tip and tissue. A lumen extends through the catheter body and the distal tip and having one more openings corresponding to the one or more ports on the distal tip. One or more optical fibers are configured to extend through the lumen and the one or more openings to an outer surface of the distal tip through one or more ports in the distal tip such that the one or more optical fibers direct the light energy to and from the tissue through the one or more ports. The method further includes illuminated the tissue through the one or more ports in the distal tip of the catheter to excite nicotinamide adenine dinucleotide hydrogen (NADH) in an area of the tissue including ablated cardiac tissue and non-ablated tissue, collecting light reflected from the tissue through the one or more openings and directing the collected light to a light measuring instrument, imaging the area of the tissue to detect NADH fluorescence of the area of the cardiac tissue, and producing a display of the imaged, illuminated tissue, the display illustrating the ablated cardiac tissue as having less fluorescence than non-ablated tissue.

In some embodiments, the method can further include ablating tissue with the distal tip prior to imaging the tissue. In some embodiments, the method can further include ablating additional non-ablated tissue identified by distinguishing between the ablated tissue and the non-ablated tissue based on the amount of fluorescence. In some embodiments, the tissue is selected from a group consisting of skeletal muscle, liver, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, genitourinary, and kidney.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure generally relates to systems and methods for imaging tissue using nicotinamide adenine dinucleotide hydrogen (NADH) fluorescence (fNADH). By way of a non-limiting example, the present systems and methods can be used in connection with ablation therapy. In some embodiments, the catheter can be used to for applying energy, such as radiofrequency, pulsed field, modulated, laser or cryo ablation energy, to the body to form therapeutic lesions.

In general, the system can include a catheter with an optical system for exchanging light between tissue and the catheter. In some embodiments, the instant systems allow for direct visualization of the tissue's NADH fluorescence, or lack thereof, induced by ultraviolet (UV) excitation. The fluorescence signature returned from the tissue can be used to determine the presence or absence of ablation lesions in illuminated tissue as well as information about a lesion as it is forming during ablation. This optical tissue interrogation can be performed on various tissue types, including, without limitation, various cardiac tissues, endocardial tissue, epicardial tissue, myocardium tissue, valves, vascular structures, and fibrous and anatomical structures. The systems and methods of the present disclosure may be used to analyze tissue composition including, but not limited to the presence of collagen and elastin. However, the presently disclosed methods and systems may also be applicable for analyzing lesions in other tissue types, for example, skeletal muscle, liver, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, genitourinary, kidney, and uterine. For example, the systems and methods described herein can also be used in urological applications, such as for ablation of kidney to treat kidney cancer. The lesions to be analyzed may be created by application of ablation energy during the ablation procedure. In some embodiments, existing lesions, created by ablation or by other means, may also be analyzed using methods and systems disclosed herein.

Figure 1:
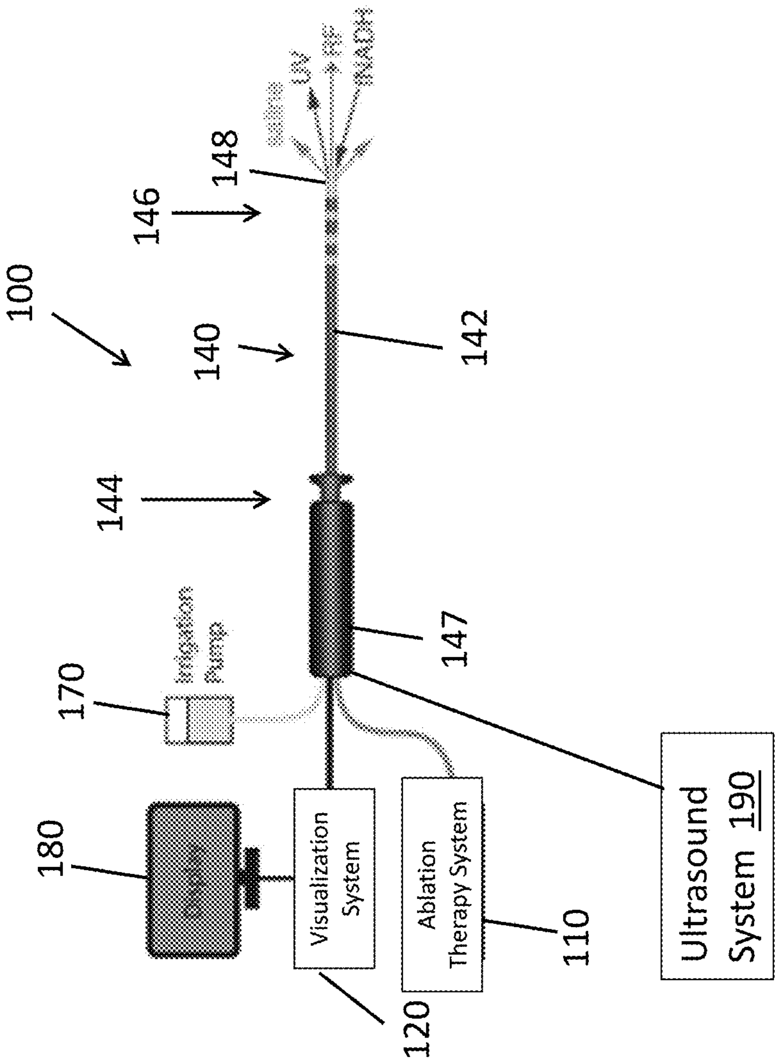
FIG. 1 is an embodiment of an ablation visualization system of the present disclosure.

In reference to FIG. 1, the system for providing ablation therapy 100 may include an ablation therapy system 110, a visualization system 120, and a catheter 140. In some embodiments, the system 100 may also include an irrigation system 170. The system may also include a display 180, which can be a separate display or a part of the visualization system 120, as described below.

In some embodiments, the ablation therapy system 110 is designed to supply ablation energy to the catheter 140. The ablation therapy system 110 may include one or more energy sources that can generate radiofrequency (RF) energy, microwave energy, electrical energy (for example, pulsed field ablation), electroporation, electromagnetic energy, cryoenergy, laser energy, ultrasound energy, acoustic energy, chemical energy, thermal energy or any other type of energy that can be used to ablate tissue.

In some embodiments, the system includes an RF generator, an irrigation pump 170, an irrigated-tip ablation catheter 140, and the visualization system 120.

Figure 2A:
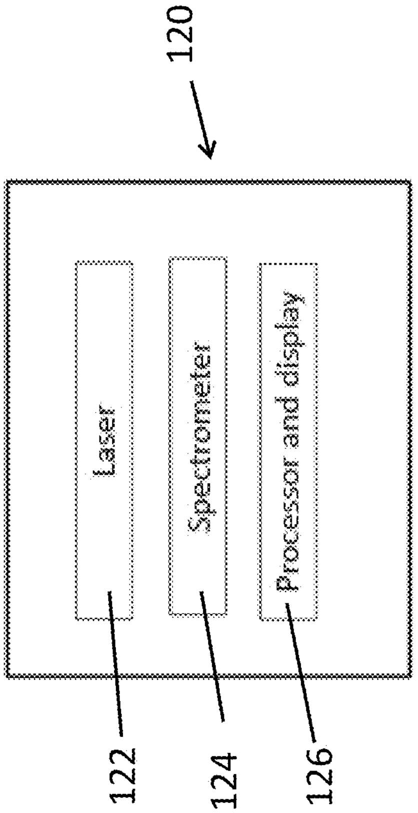
FIG. 2A is a diagram of a visualization system for use in connection with an ablation visualization system of the present disclosure.

In reference to FIG. 2A, the visualization system 120 may include a light source 122, a light measuring instrument 124, and a computer system 126.

Figure 2B:
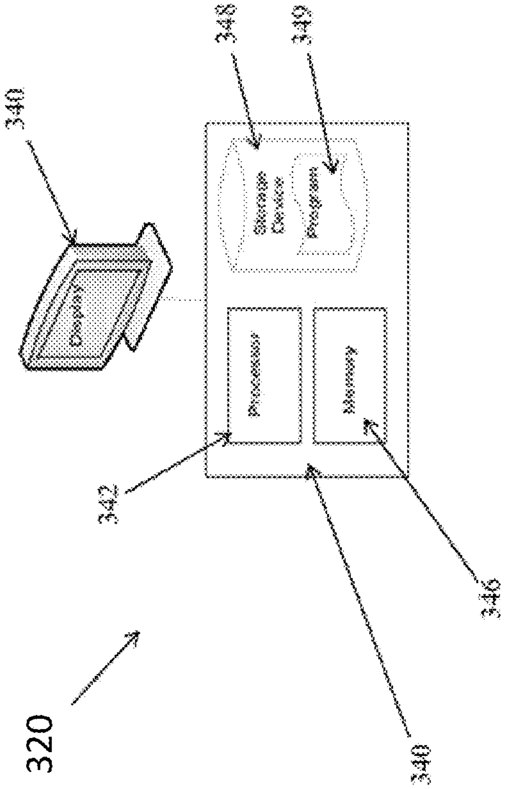
FIG. 2B illustrates an exemplary computer system suitable for use in connection with the systems and methods of the present disclosure.

The computer system 126 can be programed to control various modules of the system 100, including, for example, control over the light source 122, control over the light measuring instrument 124, execution of application specific software, control over ultrasound, navigation and irrigation systems and similar operations. FIG. 2B shows, by way of example, a diagram of a typical processing architecture 320, which may be used in connection with the methods and systems of the present disclosure. A computer processing device 340 can be coupled to display 340AA for graphical output. Processor 342 can be a computer processor 342 capable of executing software. Typical examples can be computer processors (such as Intel® or AMD® processors), ASICs, microprocessors, and the like. Processor 342 can be coupled to memory 346, which can be typically a volatile RAM memory for storing instructions and data while processor 342 executes. Processor 342 may also be coupled to storage device 348, which can be a non-volatile storage medium, such as a hard drive, FLASH drive, tape drive, DVDROM, or similar device. Although not shown, computer processing device 340 typically includes various forms of input and output. The I/O may include network adapters, USB adapters, Bluetooth® radios, mice, keyboards, touchpads, displays, touch screens, LEDs, vibration devices, speakers, microphones, sensors, or any other input or output device for use with computer processing device 340. Processor 342 may also be coupled to other types of computer-readable media, including, but not limited to, an electronic, optical, magnetic, or other storage or transmission device capable of providing a processor, such as the processor 342, with computer-readable instructions. Various other forms of computer-readable media can transmit or carry instructions to a computer, including a router, private or public network, or other transmission device or channel, both wired and wireless. The instructions may comprise code from any computer- programming language, including, for example, C, C++, C #, Visual Basic, Java, Python, Perl, and JavaScript.

Program 349 can be a computer program or computer readable code containing instructions and/or data and can be stored on storage device 348. The instructions may comprise code from any computer-programming language, including, for example, C, C++, C#, Visual Basic, Java, Python, Perl, and JavaScript. In a typical scenario, processor 342 may load some or all of the instructions and/or data of program 349 into memory 346 for execution. Program 349 can be any computer program or process including, but not limited to web browser, browser application, address registration process, application, or any other computer application or process. Program 349 may include various instructions and subroutines, which, when loaded into memory 346 and executed by processor 342 cause processor 342 to perform various operations, some or all of which may effectuate the methods for managing medical care disclosed herein. The program 349 may be stored on any type of non-transitory computer readable medium, such as, without limitation, hard drive, removable drive, CD, DVD or any other type of computer-readable media.

In some embodiments, the computer system may be programmed to perform the steps of the methods of the present disclosure and control various parts of the instant systems to perform necessary operation to achieve the methods of the present disclosure. In some embodiments, the processor may be programed to receive NADH fluorescence data from a tissue illuminated with UV light through the distal tip of the catheter, wherein the tissue is illuminated in a radial direction, an axial direction, or both; to determine from a level of NADH fluorescence in the illuminated tissue when the distal tip of the catheter is in contact with the tissue; and to cause (either automatically or by prompting the user) delivery of ablation energy to the tissue to form a lesion in the tissue upon determining that the distal tip is in contact with the tissue.

The processor may further be programmed for monitoring the level of NADH fluorescence during the delivering ablation energy to confirm that the distal tip remains in contact with the tissue. In some embodiments, monitoring the level of NADH fluorescence during the delivery of ablation energy may be utilized to determine stability of contact between the distal tip and the tissue. In some embodiments, ablation of the tissue may be stopped when the contact between the distal tip and the tissue is not stable. In some embodiments, the processor may further be programmed to collect a spectrum of fluorescence light returned from the illuminated tissue to distinguish tissue type.

In some embodiments, the light source 122 may have an output wavelength within the target fluorophore (NADH, in some embodiments) absorption range in order to induce fluorescence in healthy myocardial cells. In some embodiments, the light source 122 is a solid-state laser that can generate UV light to excite NADH fluorescence. In some embodiments, the wavelength may be about 355 nm or 355 nm+/−30 nm. In some embodiments, the light source 122 can be a UV laser. Laser-generated UV light may provide much more power for illumination and may be more efficiently coupled into a fiber-based illumination system, as is used in some embodiments of the catheter. In some embodiments, the instant system can use a laser with adjustable power up to 150 mW.

The wavelength range on the light source 122 may be bounded by the anatomy of interest, a user specifically choosing a wavelength that causes maximum NADH fluorescence without exciting excessive fluorescence of collagen, which exhibits an absorption peak at only slightly shorter wavelengths.

The wavelength range on the light source 122 may be bounded by the anatomy of interest, a user specifically choosing a wavelength that causes maximum NADH fluorescence without exciting excessive fluorescence of collagen, which exhibits an absorption peak at only slightly shorter wavelengths. In some embodiments, the light source 122 generates light having at least one wavelength between 250 nm and 450 nm. In some embodiments, the light source 122 generates light having at least one wavelength between 300 nm and 400 nm. In some embodiments, the light source 122 generates light having at least one wavelength between 330 nm and 385 nm. In some embodiments, the light source 122 generates light having at least one wavelength between 330 nm to 355 nm. In some embodiments, a narrow-band 355 nm source may be used. The output power of the light source 122 may be high enough to produce a recoverable tissue fluorescence signature, yet not so high as to induce cellular damage. The light source 122 may be coupled to an optical fiber to deliver light to and from the catheter 140, as will be described below.

In some embodiments, the light measuring instrument may monitor a level of the returned light having a wavelength between about 450 nm and 470 nm. In some embodiments, the monitored spectrum may be between 420 nm and 500 nm. In some embodiments, the monitored spectrum may be between 400 nm and 520 nm. Additionally or alternatively, a wider spectrum may be monitored, such as, by way of a non-limiting example, between 375 nm and 650 nm. In some embodiments, the NADH fluorescence spectrum and a wider spectrum may be displayed to user simultaneously. In some embodiments, the lesion may be created by ablation PFA energy. In some embodiments, the procedure may be started (by the processor or by prompting the user by the processor) when a NADH fluorescence peak is detected so it can be monitored throughout the procedure. As noted above, the processor may perform these methods in combination with other diagnostic methods, such as ultrasound monitoring.

In some embodiments, the systems of the present disclosure may utilize a spectrometer as the light measuring instrument 124. In some embodiments, the light measuring instrument 124 may comprise a camera connected to the computer system 126 for analysis and viewing of tissue fluorescence. In some embodiments, the camera may have high quantum efficiency for wavelengths corresponding to NADH fluorescence. One such camera is an Andor iXon DV860. The spectrometer 124 may be coupled to an imaging bundle that can be extended into the catheter 140 for visualization of tissue. In some embodiments, the imaging bundle for spectroscopy and the optical fiber for illumination may be combined. An optical bandpass filter of between 435 nm and 485 nm, in some embodiments, of 460 nm, may be inserted between the imaging bundle and the camera to block light outside of the NADH fluorescence emission band. In some embodiments, other optical bandpass filters may be inserted between the imaging bundle and the camera to block light outside of the NADH fluorescence emission band selected according to the peak fluorescence of the tissue being imaged.

In some embodiments, the light measuring instrument 124 may be a CCD (charge-coupled device) camera. In some embodiments, the spectrometer 124 may be selected so it is capable of collecting as many photons as possible and that contributes minimal noise to the image. Usually for fluorescence imaging of live cells, CCD cameras should have a quantum efficiency at about 460 nm of at least between 50-70%, indicating that 30-50% of photons will be disregarded. In some embodiments, the camera has quantum efficiency at 460 nm of about 90%. The camera may have a sample rate of 80 KHz. In some embodiments, the spectrometer 124 may have a readout noise of 8e- (electrons) or less. In some embodiments, the spectrometer 124 has a minimum readout noise of 3e-. Other light measuring instruments may be used in the systems and methods of the present disclosure.

The optical fiber 150 can deliver the gathered light to a long pass filter that blocks the reflected excitation wavelength of 355 nm but passes the fluoresced light that is emitted from the tissue at wavelengths above the cutoff of the filter. The filtered light from the tissue can then be captured and analyzed by a high-sensitivity spectrometer 124. The computer system 126 acquires the information from the spectrometer 124 and displays it to the physician. The computer 126 can also provide several additional functions including control over the light source 122, control over the spectrometer 124, and execution of application specific software.

In some embodiments, the digital image that is produced by analyzing the light data may be used to do the 2D and 3D reconstruction of the lesion, showing size, shape and any other characteristics necessary for analysis. In some embodiments, the image bundle may be connected to the spectrometer 124, which may generate a digital image of the lesion being examined from NADH fluorescence (fNADH), which can be displayed on the display 180. In some embodiment, these images can be displayed to the user in real time. The images can be analyzed by using software to obtain real-time details (e.g. intensity or radiated energy in a specific site of the image) to help the user to determine whether further intervention is necessary or desirable. In some embodiments, the NADH fluorescence may be conveyed directly to the computer system 126.

In some embodiments, the optical data acquired by the light measuring instrument can be analyzed to provide information about lesions during and after ablation including, but not limited to lesion depth and lesion size. In some embodiments, data from the light measuring instrument can be analyzed to determine if the catheter 140 is in contact with the myocardial surface and how much pressure is applied to the myocardial surface by the tip of the catheter. In some embodiments, data from the spectrometer 124 is analyzed to determine the presence of collagen or elastin in the tissue. In some embodiments, data from the light measuring instrument is analyzed and presented visually to the user via a graphical user interface in a way that provides the user with real-time feedback regarding lesion progression, lesion quality, myocardial contact, tissue collagen content, and tissue elastin content.

In some embodiments, the system 100 of the present disclosure may further include an ultrasound system 190. The catheter 140 may be equipped with ultrasound transducers in communication with the ultrasound system. In some embodiments, the ultrasound may show tissue depths, which in combination with the metabolic activity or the depth of lesion may be used to determine if a lesion is in fact transmural or not.

Referring back to FIG. 1, the catheter 140 includes a catheter body 142 having a proximal end 144 and a distal end 146. The catheter body 142 may be made of a biocompatible material and may be sufficiently flexible to enable steering and advancement of the catheter 140 to a site of ablation. In some embodiments, the catheter body 142 may have zones of variable stiffness. For example, the stiffness of the catheter 140 may increase from the proximal end 144 toward the distal end 146. In some embodiments, the stiffness of the catheter body 142 is selected to enable delivery of the catheter 140 to a desired cardiac location. In some embodiments, the catheter 140 can be a steerable, irrigated radiofrequency (RF) ablation catheter that can be delivered through a sheath to the endocardial space, and in the case of the heart's left side, via a standard transseptal procedure using common access tools. The catheter 140 may include a handle 147 at the proximal end 144. The handle 147 may be in communication with one or more lumens of the catheter to allow passage of instruments or materials through the catheter 140. In some embodiments, the handle 147 may include connections for the standard RF generator and irrigation system for therapy. In some embodiments, the catheter 140 may also include one or more adaptors configured to accommodate the optical fiber 150 for illumination and spectroscopy.

Figure 3:
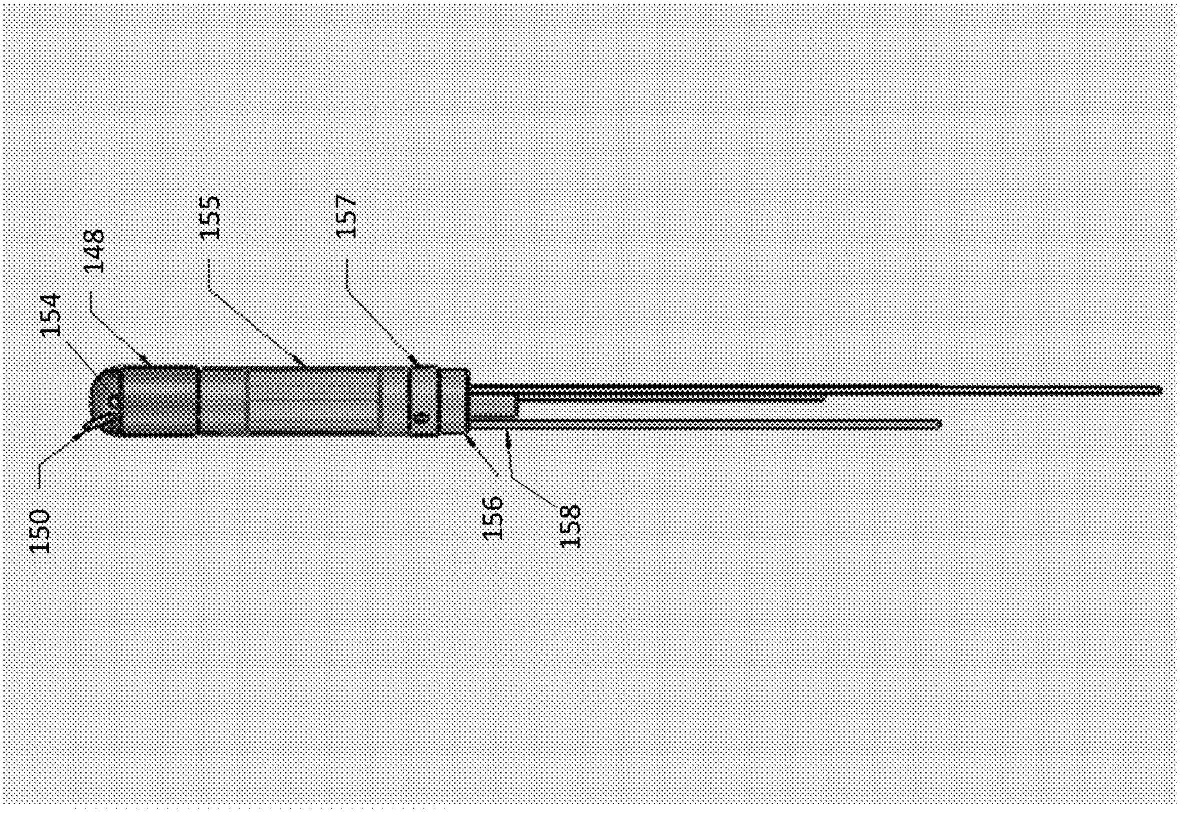
FIG. 3 illustrates an embodiment of a catheter of the present disclosure.

In reference to FIG. 3, at the distal end 146, the catheter 140 may include a distal tip 148. In some embodiments, the distal tip 148 may be configured to act as an electrode for diagnostic purposes, such as electrogram sensing, for therapeutic purposes, such as for emitting ablation energy, or both. In some embodiments where ablation energy is required, the distal tip 148 of the catheter 140 could serve as an ablation electrode or ablation element.

In the embodiments where RF energy is implemented, the wiring to couple the distal tip 148 to the RF energy source (external to the catheter) can be passed through a lumen of the catheter. The distal tip 148 may include a port in communication with the one or more lumens of the catheter. The distal tip 148 can be made of any biocompatible material. In some embodiments, if the distal tip 148 is configured to act as an electrode, the distal tip 148 can be made of metal, including, but not limited to, platinum, platinum-iridium, stainless steel, titanium or similar materials.

Figure 4:
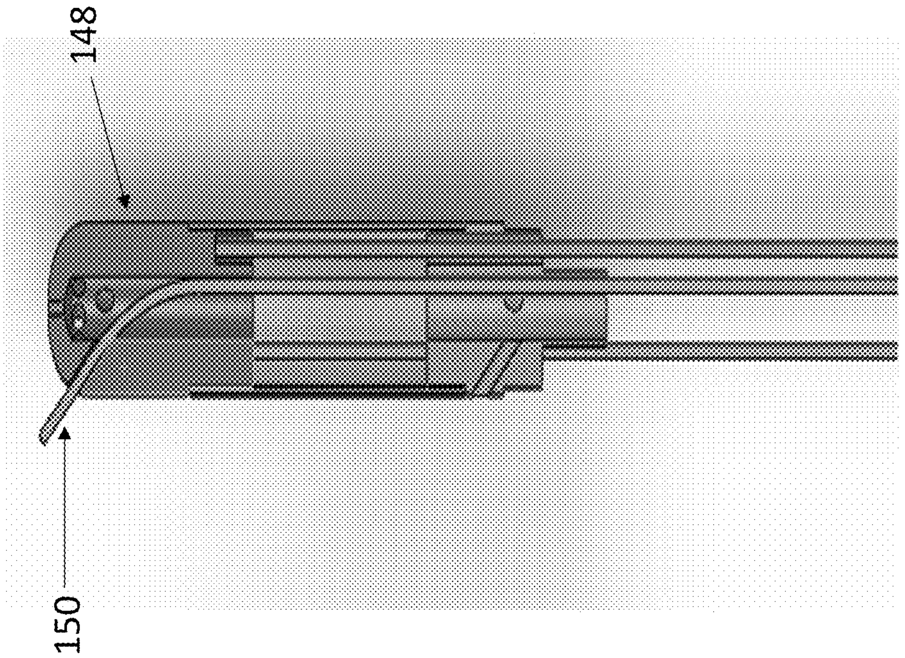
FIG. 4 illustrates an embodiment of a distal tip of the catheter shown in FIG. 3.

In reference to FIG. 3 and FIG. 4, an optical fiber or an imaging bundle may be passed from the visualization system 120, through the catheter body 142, and into an illumination cavity or compartment, defined by the distal tip 148. The distal tip 148 can be provided with one or more openings 154 for exchange of light energy between the illumination cavity and tissue. In some embodiments, even with multiple openings 154, the function of the distal tip 148 as an ablation electrode is not compromised. This light is delivered by one or more fibers 150 to the distal tip 148, where it illuminates the tissue in the proximity of the distal tip 148. This illumination light is either reflected or causes the tissue to fluoresce. The light reflected by and fluoresced from the tissue may be gathered by the optical fiber 150 within the distal tip 148 and carried back to the visualization system 120. In some embodiments, the same optical fiber or bundle of fibers 150 may be used to direct light to the tissue such that each fiber is coupled to each opening 154 to illuminate tissue outside the catheter 140 in one or more directions and to collect light from the tissue.

In some embodiments, the one or more openings 154 may be provided in any location on the walls of the distal tip 148. In some embodiments, the one or more openings 154 may be disposed circumferentially along the distal tip 148 around the entire circumference of the distal tip 148. In some embodiments, the one or more openings 154 may be disposed equidistantly from one another. The number of the openings may be determined by the desired angle of viewing coverage. For example, with 3 openings equally spaced, illumination and returned light occur at 120-degree increments (360 degrees divided by 3). In some embodiments, the one or more openings 154 may be provided in multiple rows along the walls of the distal tip 148. In some embodiments, the distal tip 148 may include 3 or 4 openings. In some embodiments, a single opening may be provided. In some embodiments, multiple openings 154 may be provided in the distal tip. In some embodiments, the distal tip 148 is provided with 3 side openings and 1 front opening. The one or more openings 154 may also serve as an irrigation port in connection with the irrigation system. In some embodiments light is only directed through some of the side openings 154. For example, in some embodiments there may exist 6 openings in the side wall, but light may be directed through only 3 of the openings, while the other openings may be used for irrigation. In some embodiments, the distal tip can include a flexible joint/irrigation line 155 for delivering fluid for irrigation. TC and RF wires 158 can pass through a ring 156 potted to allow for irrigation, and a first electrode/second fiber ring 157 can be oriented to the first ring 156.

To enable the light energy exchange between the distal tip of the catheter and tissue over multiple paths (axially and radially with respect to the longitudinal central axis of the catheter), one or more fibers 150 are positioned in the distal tip of the catheter. In some embodiments, each fiber is configured to be coupled to one of a plurality of openings in the distal tip 148, as shown in more detail in FIG. 4. While FIG. 4 illustrates a single fiber 150, it will be understood that this is for illustrative purposes only and that any number of fibers can be used. As shown in FIG. 4, the one or more optical fibers pass through the catheter to the distal tip thereof. A distal end of the fiber can be positioned such that it passes through one of the openings in the distal tip to direct light energy to tissue. It is possible that each fiber can be positioned through each opening, or there can be additional openings in the distal tip that can be used, for example, for irrigation or other functions.

Figure 5:
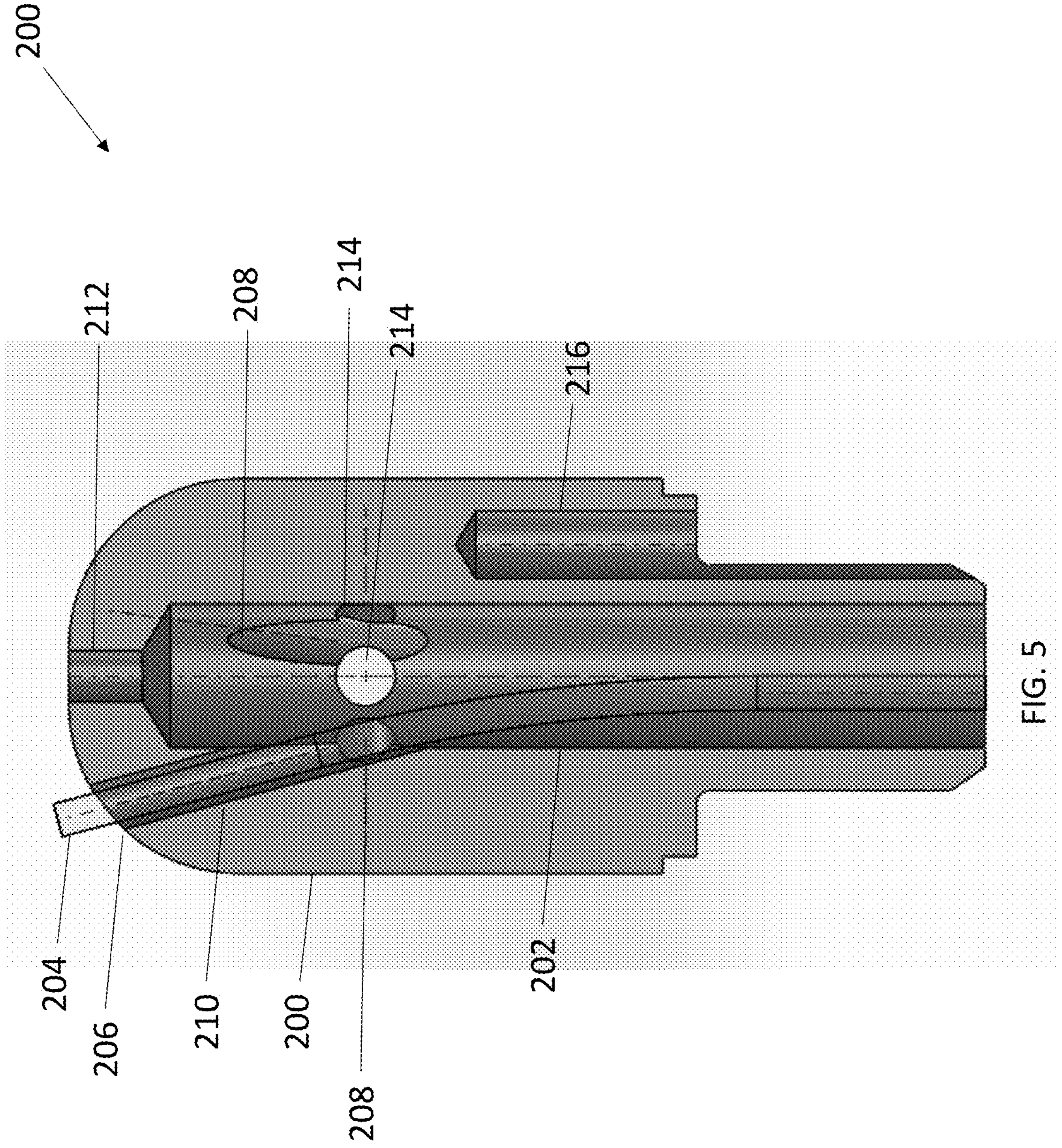
FIG. 5 illustrates an embodiment of a distal tip of a catheter.

In some embodiments, the fibers are placed through the lumens in the tip with excess fiber. The fiber is then adhered to the tip typically using low or non-fluorescent epoxy. The excess fiber and any excess adhering compound can be trimmed at the outer surface of the tip and the fiber is then polished. The tip in FIG. 5 shows the excess fiber protruding from the tip before trimming. The fibers can be distributed around the tip in three dimensions to form as many light ports as any application would require. In some embodiments, full radial coverage with can be achieved with three radial ports separated at 120 degrees circumferentially around the catheter tip.

FIG. 5 illustrates an embodiment of a distal tip of a catheter for ablating tissue. As shown in FIG. 5, the distal tip 200 includes a lumen 202 for passing one or more optical fibers 204 and fluid through the catheter and into the distal tip 200. While the lumen 202 is shown as a single lumen, more than one lumen used such that there can be separate lumens for the optical fibers and the fluid.

The distal tip 200 can be provided with one or more openings 206 for exchange of light energy between the distal tip and tissue. This light is delivered by the one or more optical fibers 204 to the distal tip 148, where it illuminates the tissue in the proximity of the distal tip 148. Similar to the distal tip as described above, the illumination light is either reflected or causes the tissue to fluoresce, and the light reflected by and fluoresced from the tissue may be gathered by the optical fiber 204 and carried back to the visualization system 120. In some embodiments, the same optical fiber or bundle of fibers may be used to direct light to the tissue such that each fiber is coupled to each opening to illuminate tissue in one or more directions and to collect light from the tissue. A variety of configuration of openings can be positioned around the distal tip, including openings in a plurality of rows. The openings can be spaced randomly or evenly around the circumference of the distal tip. In some embodiments, there can be a combination of radial ports positioned around the circumference of the distal top, and forward-facing ports positioned at the distal end of the distal tip. For example, three radial openings can be positioned around the circumference of the distal tip, and the three openings can be evenly spaced with 120 degrees between each opening to provide full radial coverage. In some the openings can be arranged in multiple rows, with each row having openings positioned around the circumference of the distal tip. The three openings can be positioned in a single row or can be staggered along the length of the distal tip. In some embodiments, an opening 212 can be formed on the end of the distal top to allow for a forward-facing fiber to be used. The opening can be formed through the distal tip such that a channel is formed that extend between a distal end of the lumen and a distal end of the distal tip.

The shape of the distal tip can vary. As shown in FIG. 5, the distal tip is cylindrical in shape with substantially parallel walls. The distal end of the distal tip can be curved such that the distal end of the distal tip is slightly tapered. The ports or openings for the optical fibers can be positioned anywhere on the distal tip, but, as shown in FIG. 5, in some embodiments, the radial ports or openings can be located on the curved portion of the distal tip, and the forward-facing port or opening is centered at the distal end of the distal tip.

Each opening 206 on the surface of the distal tip 200 can have a corresponding opening 208 in the lumen 202 such that an optical fiber can pass from the lumen, through one or more channels 210 formed in the distal tip, and to the openings 206 on the surface of the distal tip. In some embodiments, the distal tip 200 is a solid structure and the channels 210 can be formed by drilling through the distal tip from the lumen to the surface of the distal tip. The location, length, and angle of the channels formed between the lumen and the surface can vary depending on the location of the openings 208 in the lumen and the openings 206 in the surface of the distal tip. In some embodiments, the lumen can have additional openings to allow fluid to flow out of the lumen. As shown in FIG. 5, the lumen includes one or more fluid or irrigation ports that allow fluid to pass from the lumen to the tissue through channels formed through the distal tip. While the irrigation ports and corresponding channels and openings in the surface of the distal tip can be positioned anywhere along the distal tip, in some embodiments the irrigation ports are positioned between the openings 206.

A lumen 216 can also be include that is used to pass an energy-conducting element though the catheter and into the distal tip to connect the distal tip to an ablation system. The energy-conducting element can be used to delivery any type of ablation energy to the distal tip. For example, the energy-conduction element can be in the form of an electrode, such as an RF electrode. In some embodiments, the distal tip can be formed from a material that is configured to conduct energy, such as a metal, such that the distal tip can conduct the energy delivered through the lumen 216 by the energy-conducting element.

Figure 6:
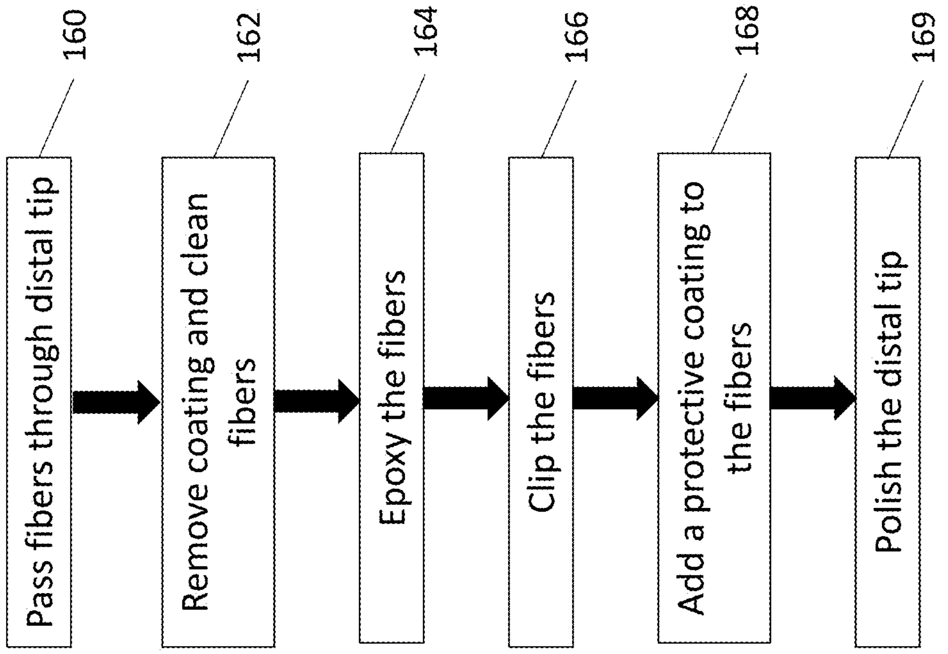
FIG. 6 illustrate an exemplary flowchart of a method for forming a distal tip of a catheter.
Figure 7:
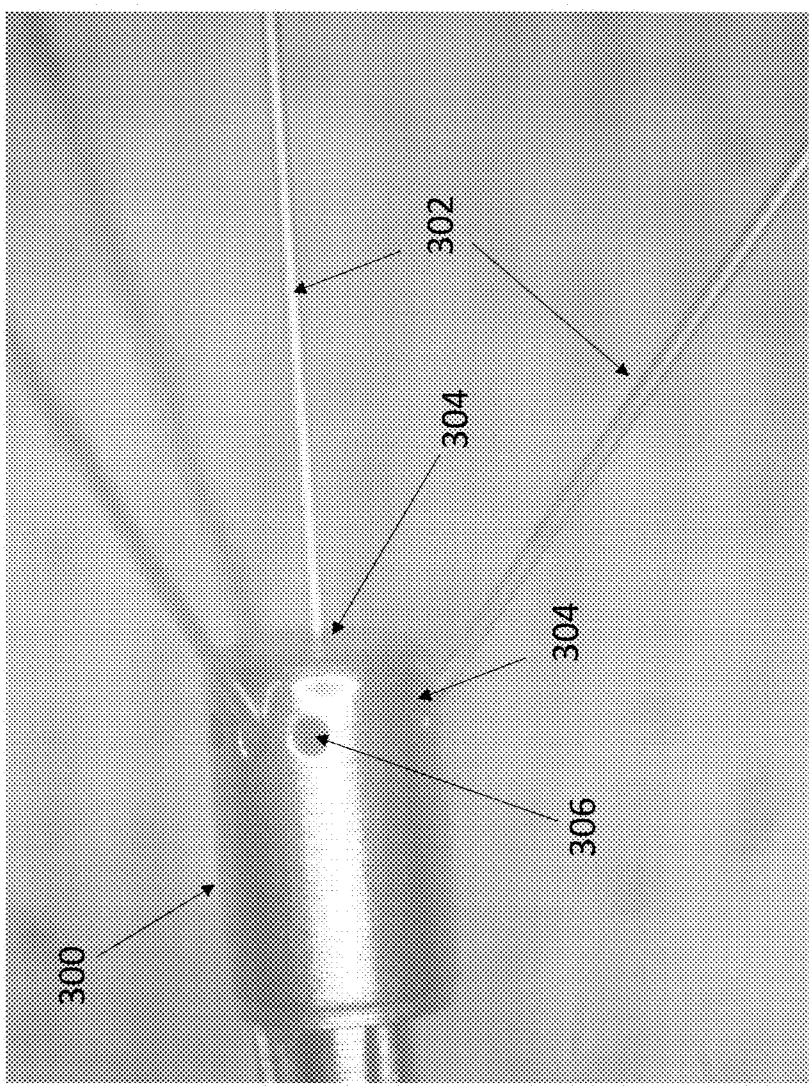
FIG. 7, FIG. 8, FIG. 9, FIG. 10, FIG. 11, and FIG. 12 illustrate exemplary images of the steps shown in FIG. 6 for forming the distal tip of the catheter.
Figure 8:
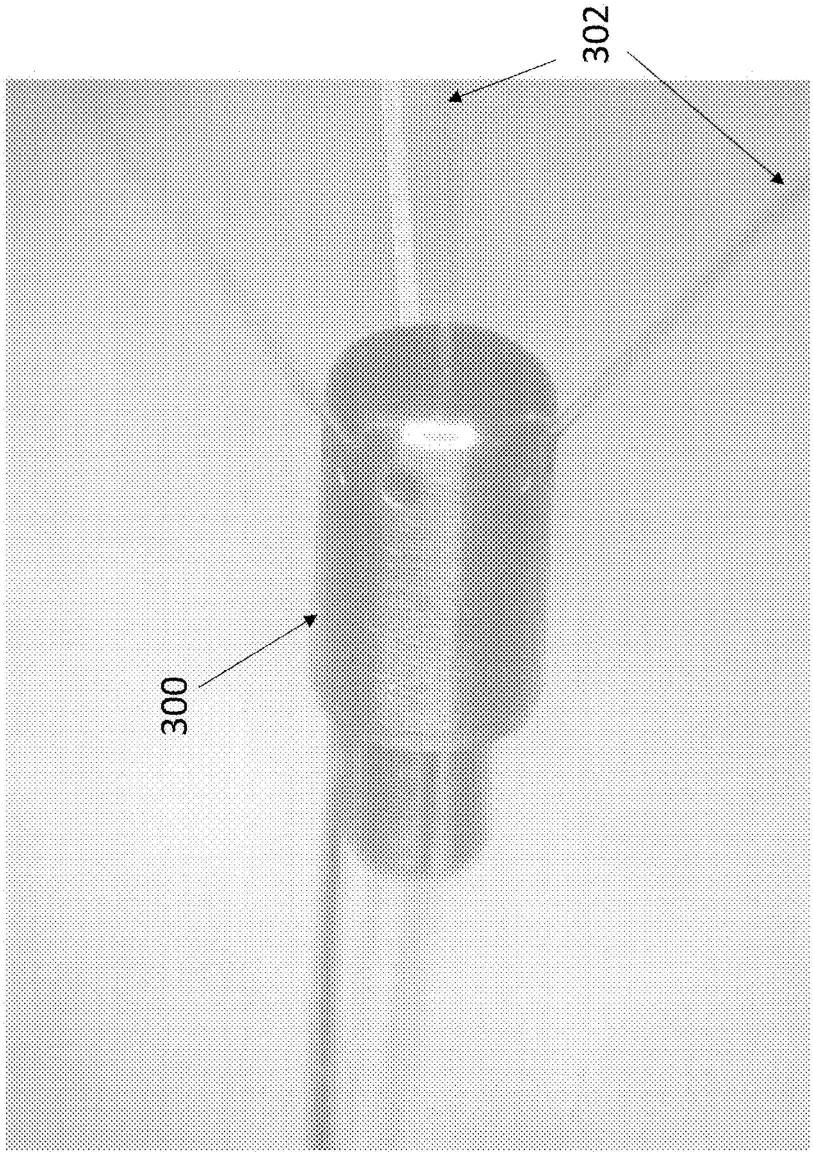
Figure 9:
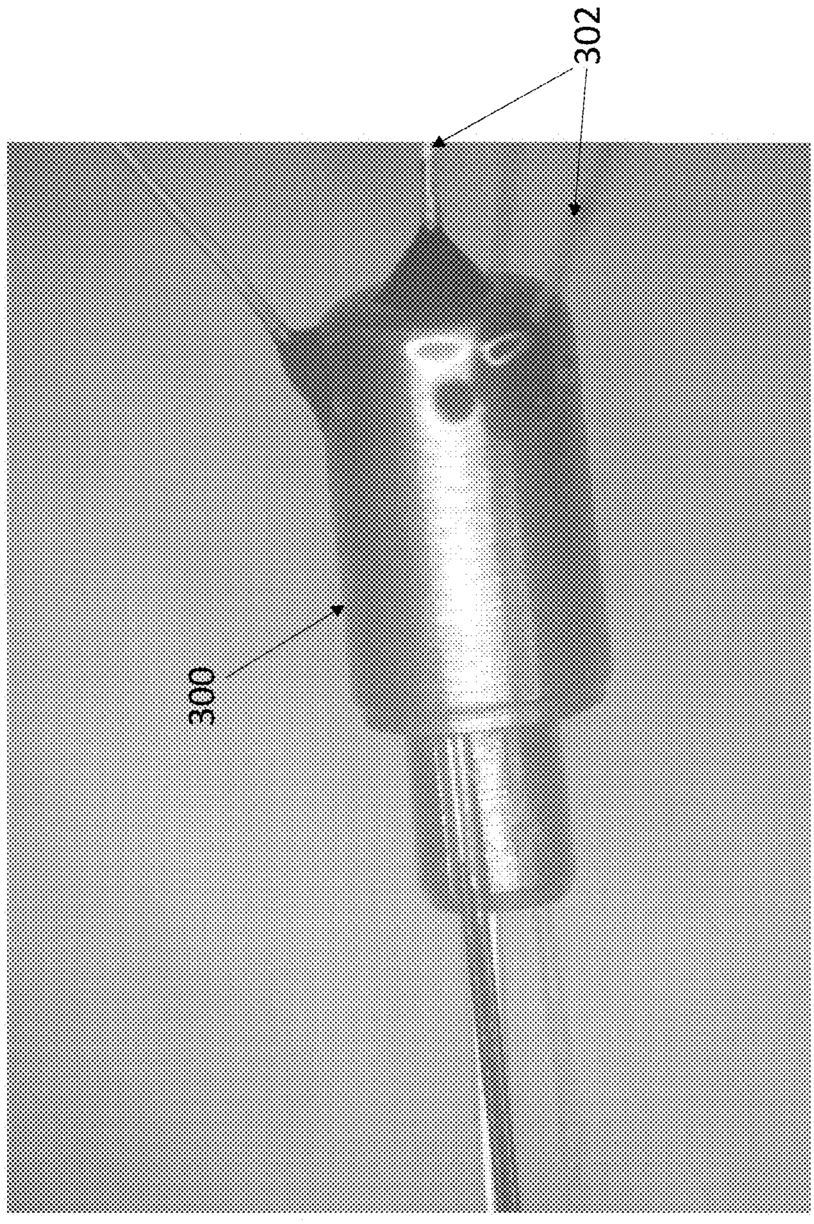
Figure 10:
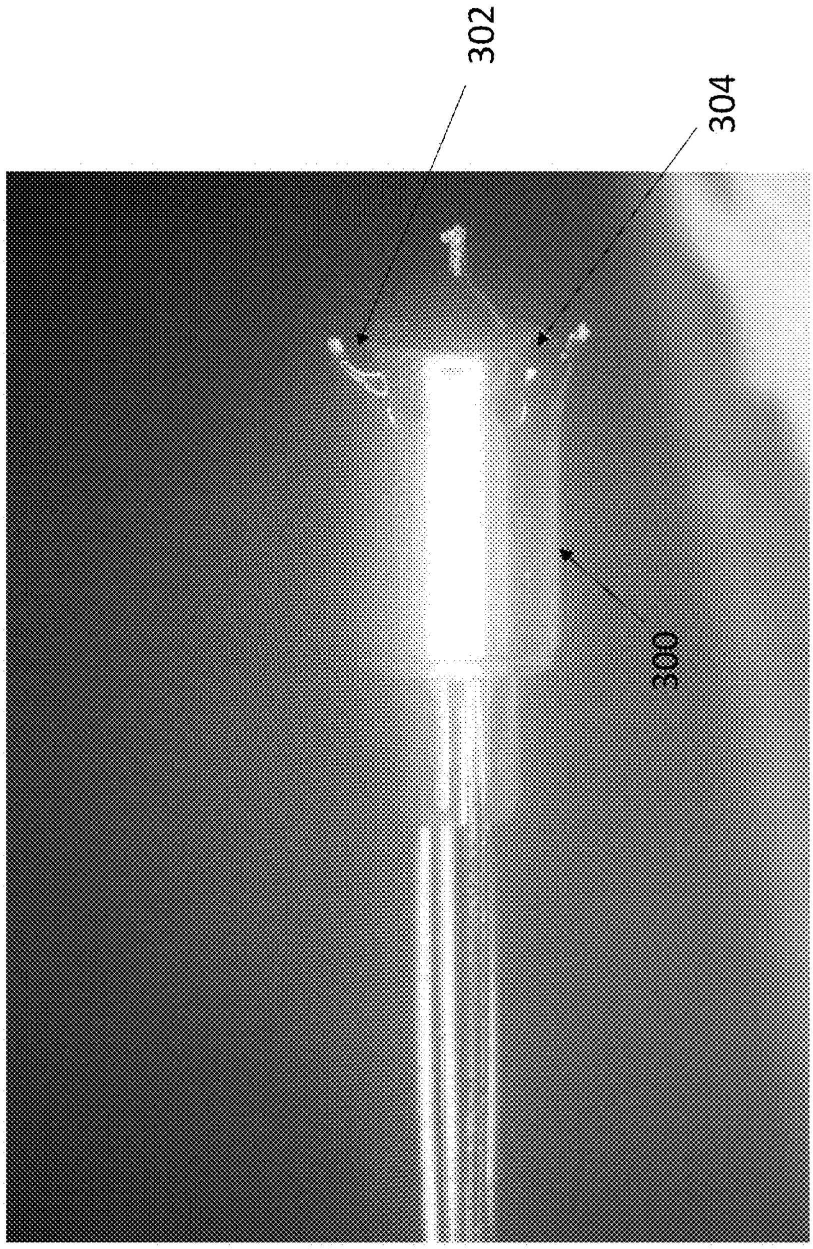
Figure 11:
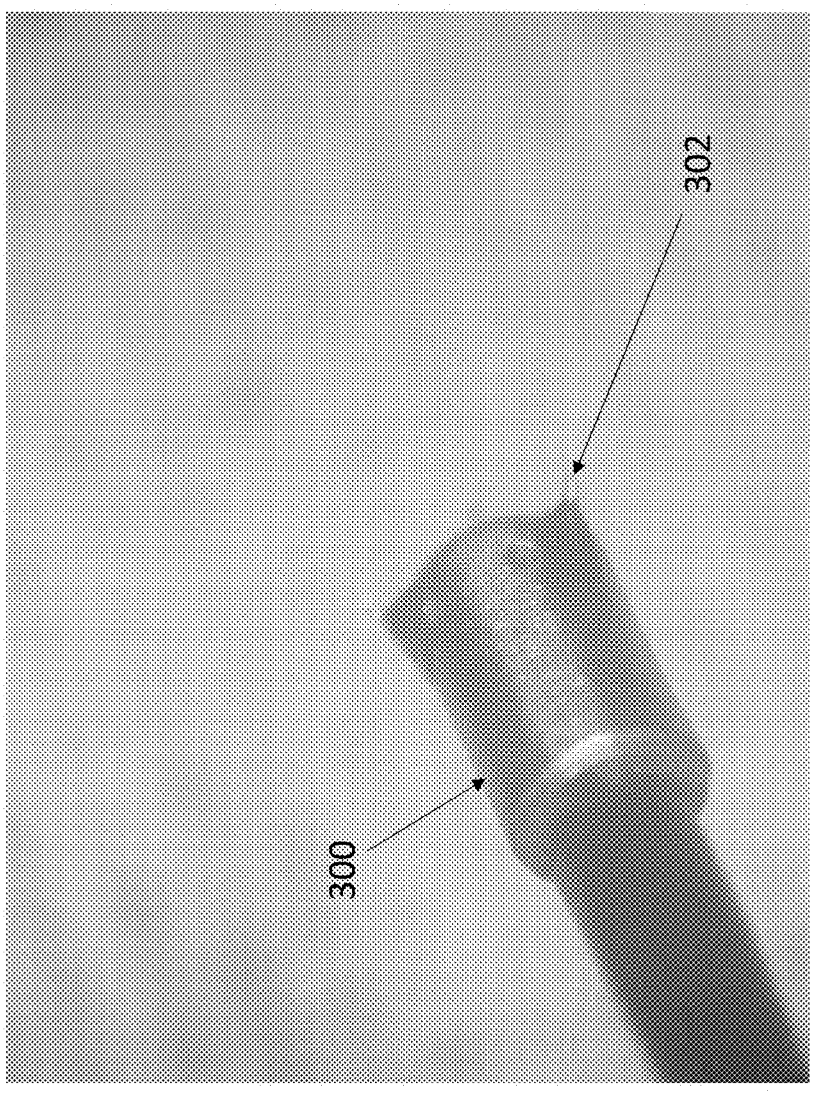
Figure 12:
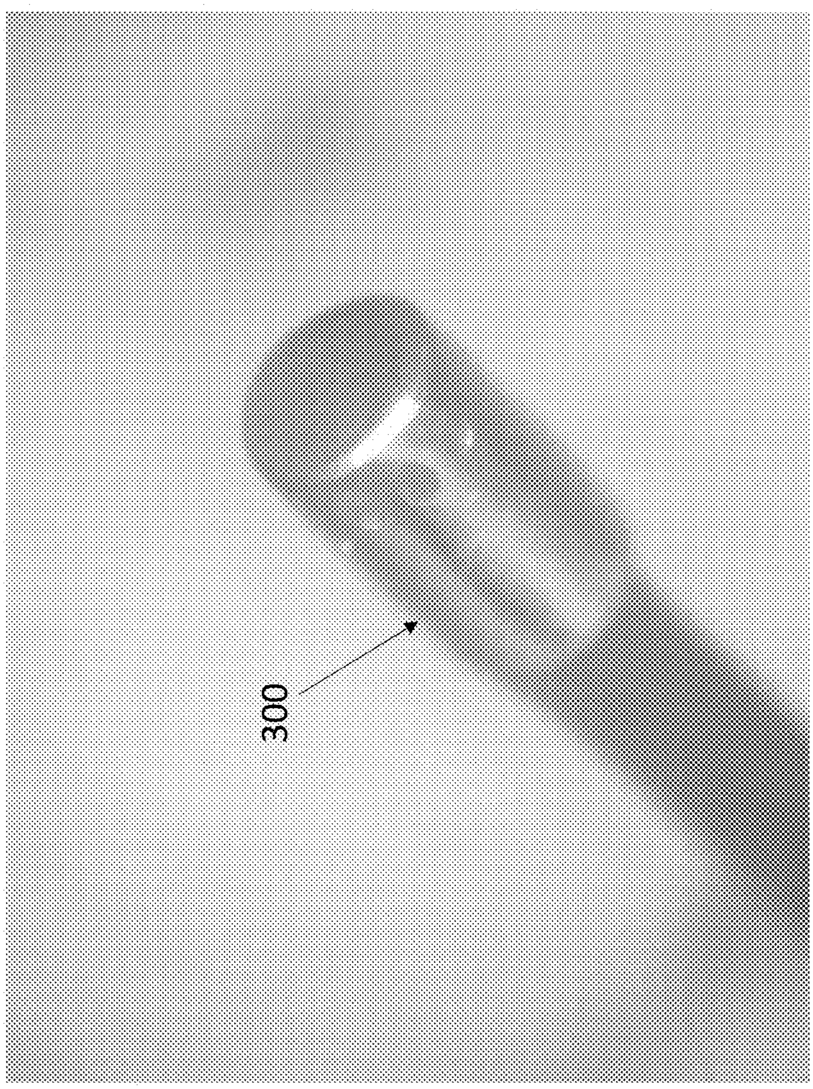

FIG. 6 illustrates an exemplary method for forming the distal tip of a catheter with one or more fibers being coupled to one or more openings therein. In step 160, one or more fibers 302 are passed through a distal tip 300, as shown in the image in FIG. 7. As shown in FIG. 7, there are a plurality of ports or openings 304 in the distal tip 300, including radial ports and a forward-facing port, through which the one or more fibers 302 extend. The distal tip 300 also includes one or more irrigation ports 306. In step 162, a coating is removed from the one or more fibers 302 and the fibers are cleaned, as shown in the image in FIG. 8. In step 164, epoxy is added to the one or more fibers 302, as shown in the image in FIG. 9. In step 166, the one or more fibers 302 are clipped such that the fibers end adjacent the openings 304 in the distal tip 300, as shown in the image in FIG. 10. In step 168, a protective coating, such as nylon, is added to the one or more fibers 302, as shown in the image in FIG. 11. In step 169, the distal tip 300 is polished, as shown in the image in FIG. 12.

As noted above, the system 100 may also include an irrigation system 170. In some embodiments, the irrigation system 170 pumps saline into the catheter to cool the tip electrode during ablation therapy. This may help to prevent steam pops and char (i.e. clot that adheres to the tip that may eventually dislodge and cause a thrombolytic event) formation. For the proposed optical system, the fluid flow may clear the opening in the distal tip 148 of any blood that otherwise would otherwise absorb the illumination light.

The irrigation system 170 may be connected to the one or more openings in the distal tip 148 and can be used, for example, for flushing the openings with fluid to clear the tip of blood, cooling the tissue-electrode interface, prevention of thrombus formation, among many other possible uses. In some embodiments, the irrigation fluid is maintained at a positive pressure relative to pressure outside of the catheter for continuous flushing of the one or more openings 154.

Figure 13:
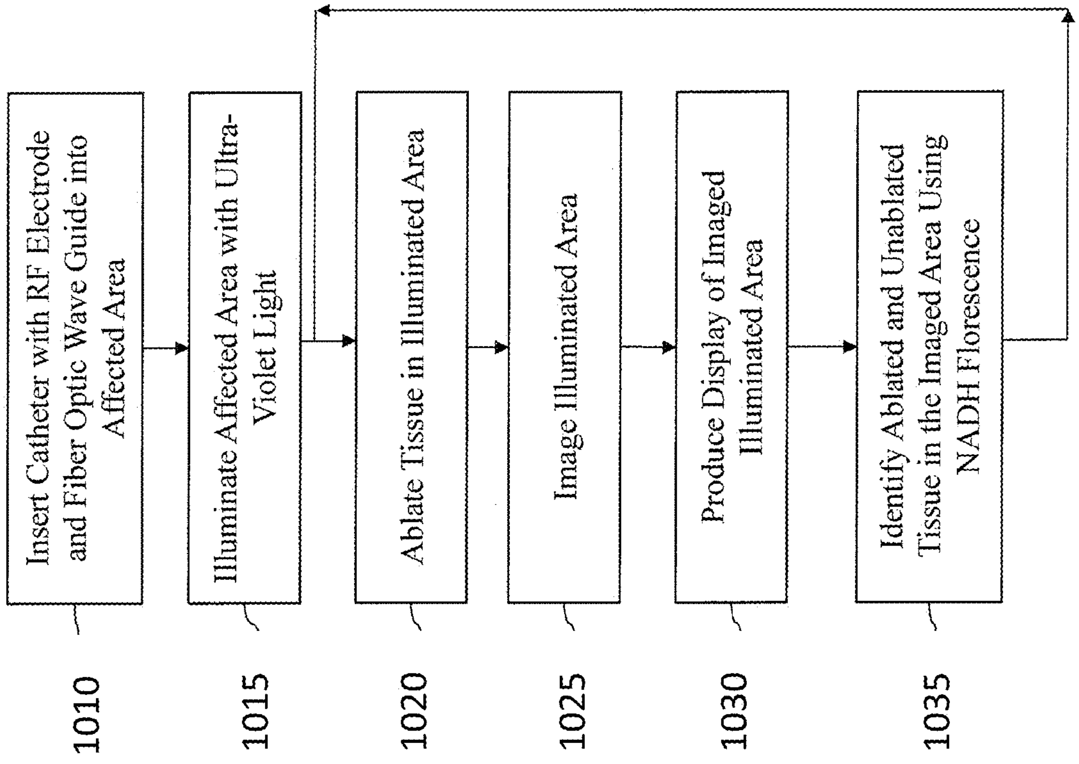
FIG. 13 is an exemplary flow chart of a method of using a system of the present disclosure.

In reference to FIG. 13, operation of the systems 100 of the present disclosure is illustrated. Initially, the catheter 140 is inserted into the area of heart tissue affected by the atrial fibrillation, such as the pulmonary vein/left atrial junction or another area of the heart (step 1010). Blood may be removed from the visual field, for example, by irrigation. The affected area may be illuminated by ultra-violet light reflected from the light directing member 160 (step 1015). Tissue in the illuminated area may be ablated (step 1020), either before, after, or during illumination. Either point-to-point RF ablation or cryoablation or laser or other known ablation procedures may be employed using the systems of the present disclosure.

Still referring to FIG. 13, the illuminated area may be imaged with the light directing member receiving the light from the tissue and directing such light to the optical fiber, which can then pass the light to the spectrometer (step 1025). In some embodiments, the methods of the present disclosure rely on imaging of the fluorescence emission of NADH, which is a reduced form of nicotinamide adenine dinucleotide (NAD+). NAD+ is a coenzyme that plays important roles in the aerobic metabolic redox reactions of all living cells. It acts as an oxidizing agent by accepting electrons from the citric acid cycle (tricarboxylic acid cycle), which occurs in the mitochondrion. By this process, NAD+ is thus reduced to NADH. NADH and NAD+ are most abundant in the respiratory unit of the cell, the mitochondria, but are also present in the cytoplasm. NADH is an electron and proton donor in mitochondria to regulate the metabolism of the cell and to participate in many biological processes including DNA repair and transcription.

By measuring the UV-induced fluorescence of tissue, it is possible to learn about the biochemical state of the tissue. NADH fluorescence has been studied for its use in monitoring cell metabolic activities and cell death. Several studies in vitro and in vivo investigated the potential of using NADH fluorescence intensity as an intrinsic biomarker of cell death (either apoptosis or necrosis) monitoring. Once NADH is released from the mitochondria of damaged cells or converted to its oxidized form (NAD+), its fluorescence markedly declines, thus making it very useful in the differentiation of a healthy tissue from a damaged tissue. NADH can accumulate in the cell during ischemic states when oxygen is not available, increasing the fluorescent intensity. However, NADH presence disappears all together in the case of a dead cell. The following table summarizes the different states of relative intensity due to NADH fluorescence:

| Cellular State | NADH Presence | Relative Changes of Auto-fluorescense intensity |
|---|---|---|
| Metabolically Active | Normal | Baseline |
| Metabolically Active but Impaired (Ischemia) | Increased due to Hypoxia | Increased |
| Metabolically Inactive (Necrotic) | Reduced | Reduced Attenuation |

Still referring to FIG. 13, while both NAD+ and NADH absorb UV light quite readily, NADH is autofluorescent in response to UV excitation whereas NAD+ is not. NADH has a UV excitation peak of about 340-360 nm and an emission peak of about 460 nm. In some embodiments, the methods of the present disclosure may employ excitation wavelengths between about 330 to about 370 nm. With the proper instrumentation, it is thus possible to image the emission wavelengths as a real-time measure of hypoxia as well as necrotic tissue within a region of interest. Furthermore, in some embodiments, a relative metric can be realized with a grayscale rendering proportionate to NADH fluorescence.

Under hypoxic conditions, the oxygen levels decline. The subsequent fNADH emission signal may increase in intensity indicating an excess of mitochondrial NADH. If hypoxia is left unchecked, full attenuation of the signal will ultimately occur as the affected cells along with their mitochondria die. High contrast in NADH levels may be used to identify the perimeter of terminally damaged ablated tissue.

To initiate fluorescence imaging, NADH may be excited by the UV light from the light source, such as a UV laser. NADH in the tissue specimen absorbs the excitation wavelengths of light and emits longer wavelengths of light. The emission light may be collected and passed back to the spectrometer, and a display of the imaged illuminated area may be produced on a display (step 1030), which is used to identify the ablated and unablated tissue in the imaged area based on the amount of NADH florescence (step 1035). For example, the sites of complete ablation may appear as completely dark area due to lack of fluorescence. Accordingly, the areas of ablation may appear markedly darker when compared to the surrounding unablated myocardium, which has a lighter appearance. This feature may enhance the ability to detect the ablated areas by providing marked contrast to the healthy tissue and even more contrast at the border zone between ablated and healthy tissue. This border area is the edematous and ischemic tissue in which NADH fluorescence becomes bright white upon imaging. The border zone creates a halo appearance around the ablated central tissue.

The process may then be repeated by returning to the ablation step, if necessary, to ablate additional tissue. It should be recognized that although FIG. 13 illustrates the steps being performed sequentially, many of the steps may be performed simultaneously or nearly simultaneously, or in a different order than shown in FIG. 13. For example, the ablation, imaging and display can occur at the same time, and the identification of the ablated and unablated tissue can occur while ablating the tissue.

In some embodiments, the system of the present disclosure comprises a catheter, a light source, and a light measuring instrument. In some embodiments, the system further comprises an optical detection system having an optical detection fiber, the optical detection system being independent or immune from electrical or RF energy noise. In some embodiments, the optical detection fiber does not conduct electrically and an RF energy does not produce electromagnetic energy in a range of interest to the system.

In some embodiments, the system is adapted to optically interrogate a catheter environment in a biologic system. In some embodiments, the system is adapted to optically interrogate in real-time, via an NADH fluorescence, the catheter environment to determine or assess one or more of a complete or a partial immersion of an electrode in a blood pool. For example, the optical system can detect, by inference, that the catheter tip is completely or partially immersed in the blood pool. The reason for this is because unlike the tissue or vasculature that return a positive optical signature, the blood completely absorbs the illumination light at this wavelength and thus returns a null optical signature. This feature of complete absorption provides optical isolation and therefore noise insulation. The instrument can use this situation for optical calibration and the elimination of stray optical signatures coming from the catheter itself. In addition, the system may be used for a qualitative and or a quantitative contact assessment between a catheter tip and a tissue, a qualitative and or a quantitative assessment of a catheter contact stability, an ablation lesion formation in real time, an ablation lesion progression monitoring, a determination of when to terminate a lesion, an identification of edematous zones which usually occur on a periphery of an ablation site and which can be associated with an incomplete ablation lesion, an ablation lesion depth, a cross-sectional area of the lesion, a temperature of the lesion, a recognition of steam formation or another physiologic parameter change to predict the onset of a steam pop, a formation of a char at a tip electrode during or after the ablation lesion formation, a detection of ischemia, a detection of a level of the ischemia, an ablation lesion assessment post lesion formation, an identification of edematous zones for re-ablation since edematous zones include myocardium that is electrically stunned, and a mapping of a location of previously ablated tissue by distinguishing metabolically active tissue from metabolically inactive tissue In some embodiments, the system is adapted to optically interrogate a tissue parameter of an NADH fluorescence (fNADH).

In some embodiments, the system is adapted to optically interrogate a tissue, wherein the system analyzes parameters including a metabolic state of the tissue as well as a tissue composition of the tissue.

In some embodiments, the system is adapted to illuminate a tissue with a wavelength wherein illuminating leads to several optical responses. In some embodiments the optical responses comprises a myocardium containing NADH fluorescing if it is in a healthy metabolic state. In some embodiments, other tissues, such as collagen or elastin, fluoresce at different wavelengths, and the system uses a measurement of this information to determine a composition (i.e. collagen or elastin) of the tissue in contact with the catheter. In some embodiments the composition comprises myocardium, muscle, and myocardial structures such as valves, vascular structures, and fibrous or anatomical components. In some embodiments the composition comprises collagen, elastin, and other fibrous or support structures.

In some embodiments, a catheter of the present disclosure comprises a catheter body, a tip electrode, and one or more sensing electrodes. In some embodiments the catheter further comprises one or more zones of different flexibility, the zones of flexibility being in combination with a deflection mechanism adapted to allow a distal portion of the catheter to be bent for ease of navigation for a physician. In some embodiments, the zones of flexibility are located at the distal portion of the catheter, while a main body of the catheter is kept relatively stiff for pushability. In some embodiments, the main body of the catheter body is flexible so that the physician can use a robotic system for catheter navigation. In some embodiments the catheter is flexible and capable of being manipulated within a catheter sheath manually or robotically.

In some embodiments, the catheter further comprises a deflection mechanism adapted to deflect the catheter tip for navigation. In some embodiments the deflection mechanism comprises one or more pull wires that are manipulated by a catheter handle and which deflect the distal portion of the catheter in one or more directions or curve lengths. In some embodiments, the catheter further comprises a temperature sensor, the temperature sensor being integral to the distal tip of the electrode. In some embodiments the catheter further comprises one or more ultrasound transducers, the ultrasound transducers being located in the distal section of the catheter, and preferably in the tip of the distal electrode. The ultrasonic transducers are adapted to assess a tissue thickness either below or adjacent to the catheter tip. In some embodiments, the catheter comprises multiple transducers adapted to provide depth information covering a situation where the catheter tip is relatively perpendicular to a myocardium or relatively parallel to a myocardium.

In some embodiments the catheter further comprises an irrigation means for the purposes of flushing catheter openings with an irrigation fluid to clear the tip of blood, cooling a tissue-electrode interface, preventing a thrombus formation, and dispersing an RF energy to a greater zone of tissue, thus forming larger lesions than non-irrigated catheters. In some embodiments, the irrigating fluid is maintained within the catheter tip at a positive pressure relative to outside of the tip, and is adapted for continuous flushing of the openings.

In some embodiments, the catheter further comprises an electromagnetic location sensor adapted for locating and navigating the catheter. In some embodiments, the electromagnetic location sensor is adapted to locate the tip of the catheter in a navigation system of any one of several catheter manufacturers. The sensor picks up electromagnetic energy from a source location and computes location through triangulation or other means. In some embodiments the catheter comprises more than one transducer adapted to render a position of the catheter body and a curvature of the catheter body on a navigation system display.

In some embodiments, a catheter adapted to ablate tissue comprises a catheter body, and a tip electrode adapted to ablate a tissue. In some embodiments the catheter further comprises at least one optical waveguide adapted to deliver light energy to the tissue, and one or more optical waveguides adapted to receive light energy from the tissue. In some embodiments, the catheter further comprises a single optical waveguide adapted to deliver light energy to the tissue and receive light energy from the tissue.

In some embodiments, the catheter is adapted for an ablation energy, the ablation energy being one or more of RF energy, cryo energy, laser energy, chemical energy, electroporation energy, high intensity focused ultrasound or ultrasound energy, pulse field ablation energy, fluid modulated energy, and microwave energy.

In some embodiments, the tip of the catheter comprises a first electrode adapted for sensing electrical activity of the tissue, a second electrode adapted for transmitting or conducting ablation energy or chemical, a light directing member to direct a light in one or more directions simultaneously, one or more openings for the transmission and receiving of light energy, one or more openings for an irrigation fluid to flow from the tip, and one or more openings adapted for transmitting and receiving light as well as concomitantly flowing irrigation fluid from the tip. In some embodiments the tip of the catheter comprises an electrically conductive material, adapted to allow the first electrode to sense the electrical activity of the tissue in contact with the catheter. In some embodiments, the tip further comprises an electrode adapted for transmitting or conducting ablation energy or a chemical energy. In some embodiments, the tip is adapted to conduct RF energy to the adjacent tissue. In some embodiments, the tip comprises an optically transparent material allowing conduction of laser ablation energy to the adjacent tissue. In some embodiments, the tip comprises a plurality of holes adapted to transmit a chemical used to alter cells of the tissue or of a tissue in close proximity to the tip. In some embodiments, the openings for transmitting and receiving light are in the distal tip. In some embodiments, the tip comprises additional holes adapted to cool the tip with a fluid during an application of ablation energy.

In some embodiments, the tip further comprises at least one opening adapted to allow a directed light energy to illuminate the tissue, and to allow the light energy to return from the tissue to the catheter. In some embodiments, the tip comprises at least one opening in the distal tip for illuminating a tissue along a longitudinal axis of the catheter. In some embodiments, the light energy is directed in a manner that is dependent upon a light directing member having a central lumen allowing a portion of the light to be directed in a longitudinal direction. In some embodiments, the tip further comprises at least one opening in the distal tip for illuminating the tissue in a radial axis with respect to the catheter. In some embodiments, the tip is adapted to direct the light by splitting the primary light source into specific multiple beams using the light directing member.

In some embodiments, the primary light source is a laser, the laser adapted to send a light beam down an optical fiber to the light directing member, wherein the light beam is sent in one or more directions, including straight ahead relative to the tip, to make sure a structure adjacent to the catheter is illuminated. In some embodiments, a structure that is illuminated will transmit optical energy back to the catheter tip and to the light directing member, which in turn reflects the returned light back up the fiber to a spectrometer.

In some embodiments, the tip is configured to direct the light energy independent of any polishing of the interior of the illumination cavity. In some embodiments, the directing of light energy does not depend on the use of an interior wall of the illumination cavity.

In some embodiments, a catheter adapted to support fNADH comprising one or more ultrasound transducers. In some embodiments, the catheter is adapted to measure a wall thickness of an area of interest. In some embodiments, the catheter is adapted to assess a metabolic state of the tissue throughout the wall thickness. In some embodiments, the catheter further comprises ultrasonic transducers adapted to measure cardiac wall thickness and adapted to assess a metabolic state of the myocardium during an application of an RF energy. In some embodiments, the catheter is adapted to identify any metabolically active tissue for the purposes of identifying electrical gaps in lesions.

In some embodiments, the catheter comprises a light-directing component adapted to send light in one or more radial directions and axially simultaneously. In some embodiments, the catheter further comprises a separate or a modular component of the tip electrode, wherein an light directing member is integrated into the tip of the electrode during. In some embodiments, the light directing member has a centrally located lumen for light to pass in the axial direction.

In some embodiments, a catheter of the present disclosure comprises of a catheter body with the following components: a catheter with a distal tip positioned at a distal end of the catheter body, the distal tip defining a light chamber, the distal tip having one or more openings for exchange of light energy between the light chamber and tissue, and a the same catheter with a light directing member disposed within the light chamber, the light directing member being configured to direct the light energy to and from the tissue through the one or more openings in the distal tip. In some embodiments, the catheter comprises of one or more optical waveguides extending into the light chamber to deliver light to and from the light chamber. In some embodiments, the catheter has a light directing member and the one or more openings are configured to enable illumination of tissue in the radial and the axial directions. In some embodiments, the catheter has a distal tip that has a dome shaped front wall and straight side walls. In some embodiments, the catheter has one or more openings that are disposed along sidewalls of the distal tip. In some embodiments, the catheter has one or more openings that are disposed circumferentially along the distal tip. In some embodiments, the catheter has one or more openings that are provided in multiple rows along side walls of the distal tip. In some embodiments, the catheter has a distal tip that is comprised of a tissue ablation electrode. In some embodiments, the catheter has a light directing member that is configured to direct light radially through the one or more openings.

In some embodiments, the catheter has a light directing member that is rotatable with respect to the light chamber. In some embodiments, the catheter has a light directing member that is comprised of one or more through-holes and the distal tip is comprised of one or more openings disposed on a front wall of the distal tip to enable passage of light in longitudinal direction through the light directing member and the one or more openings of the front wall.

The foregoing disclosure has been set forth merely to illustrate various non-limiting embodiments of the present disclosure and is not intended to be limiting. Since modifications of the disclosed embodiments incorporating the spirit and substance of the disclosure may occur to persons skilled in the art, the presently disclosed embodiments should be construed to include everything within the scope of the appended claims and equivalents thereof.

The invention claimed is:

1. A catheter for visualizing ablated tissue comprising:

a catheter body;

a distal tip positioned at a distal end of the catheter body, the distal tip having a plurality of radial ports and at least one forward-facing port for an exchange of light energy between the distal tip and tissue, wherein the plurality of radial ports are disposed circumferentially along, and equidistantly apart from, one another on a sidewall of the distal tip, the sidewall having an inner surface and an outer surface such that the plurality of radial ports and the at least one forward-facing port extends between the inner surface and the outer surface;

a first lumen extending through the catheter body and sized to pass an energy-conducting element;

a second lumen extending through the catheter body, the distal tip, and up to the at least one forward-facing port, and having a plurality of openings in a sidewall of the second lumen, wherein the plurality of openings corresponding to the plurality of radial ports on the distal tip;

a plurality of channels formed at an angle in the distal tip; and one or more optical fibers extending through the second lumen, wherein each of the plurality of channels connects a respective opening of the second lumen to a respective radial port on the sidewall of the distal tip to direct the one or more optical fibers from the second lumen through the plurality of openings and into the plurality of radial ports of the distal tip, wherein each of the one or more optical fibers is fixedly coupled to a respective port in the distal tip, and wherein a distal end of each of the one or more optical fibers terminates at, the outer surface of the sidewall of the distal tip at each respective port in the distal tip such that the one or more optical fibers directly delivers the light energy to the tissue and collects light from the tissue at the same respective port.

2. The catheter of claim 1, wherein the distal tip is configured to deliver ablation energy from the energy-conducting element to the tissue.

3. The catheter of claim 2, wherein the ablation energy is selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

4. The catheter of claim 1, wherein the light energy for illuminating the tissue has at least one wavelength between 300 nm and 400 nm.

5. The catheter of claim 1, wherein the tissue is selected from a group consisting of skeletal muscle, liver, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, genitourinary, and kidney.

6. The catheter of claim 1, wherein the distal tip is configured to be coupled to the distal end of the catheter body.

7. A system for visualizing ablated tissue comprising:

a catheter comprising a catheter body; a distal tip positioned at a distal end of the catheter body, the distal tip having a plurality of radial ports and at least one forward-facing port for exchange of light energy between the distal tip and tissue, wherein the plurality of radial ports are disposed circumferentially along, and equidistantly apart from, one another on a sidewall of the distal tip, the sidewall having an inner surface and an outer surface such that the plurality of radial ports and the at least one forward-facing port extends between the inner surface and the outer surface; a first lumen extending through the catheter body and sized to pass an energy-conducting element; a second lumen extending through the catheter body, the distal tip, and up to the at least one forward-facing port, and having a plurality of openings in a sidewall of the second lumen, wherein the plurality of openings corresponding to the plurality of radial ports on the distal tip; a plurality of channels formed at an angle in the distal tip; and one or more optical fibers extending through the second lumen, wherein each of the plurality of channels connects a respective opening of the second lumen to a respective radial port on the sidewall of the distal tip to direct the one or more optical fibers from the second lumen through the plurality of openings and into the plurality of radial ports of the distal tip, wherein each of the one or more optical fibers is fixedly coupled to a respective port in the distal tip, and wherein a distal end of each of the one or more optical fibers terminates at, the outer surface of the distal tip at each respective port in the distal tip such that the one or more optical fibers directly delivers the light energy to the tissue and collects light from the tissue at the same respective port;

a light source;

a light measuring instrument; and the one or more optical fibers in communication with the light source and the light measuring instrument and configured to pass light energy from the light source for illuminating tissue outside the distal tip and the one or more optical fibers are configured to relay light energy reflected from the tissue to the light measuring instrument.

8. The system of claim 7, further comprising an ultrasound transducer.

9. The system of claim 7, further comprising a source of ablation energy in communication with the distal tip to deliver ablation energy from the energy-conducting element to the tissue.

10. The system of claim 9, wherein the ablation energy is selected from a group consisting of radiofrequency (RF) energy, microwave energy, electrical energy, electromagnetic energy, cryoenergy, laser energy, ultrasound energy, acoustic energy, chemical energy, thermal energy and combinations thereof.

11. The system of claim 7, wherein the light energy for illuminating the tissue has at least one wavelength between 300 nm and 400 nm.

12. The system of claim 7, wherein the light measuring instrument is configured to detect returned light having a wavelength between 450 nm and 470 nm is monitored.

13. The system of claim 7, wherein the distal tip is configured to be coupled to the distal end of the catheter body.

14. A method for visualizing ablated tissue comprising:

advancing a catheter to a cardiac tissue in need of ablation, the catheter comprising a catheter body; a distal tip positioned at a distal end of the catheter body, the distal tip having a plurality of radial ports and at least one forward-facing port for exchange of light energy between the distal tip and tissue, the plurality of radial ports being disposed circumferentially along, and equidistantly apart from, one another on a sidewall of the distal tip, the sidewall having an inner surface and an outer surface such that the plurality of radial ports and the at least one forward-facing port extends between the inner surface and the outer surface; a first lumen extending through the catheter body and sized to pass an energy-conducting element; a second lumen extending through the catheter body, the distal tip, and up to the at least one forward-facing port, and having a plurality of openings in a sidewall of the second lumen, wherein the plurality of openings correspond to a respective radial port on the distal tip; a plurality of channels formed at an angle in the distal tip; and one or more optical fibers extending through the second lumen, wherein each of the plurality of channels connects a respective opening of the second lumen to a respective radial port on the sidewall of the distal tip to direct the one or more optical fibers from the second lumen through the plurality of openings and into the plurality of radial ports of the distal tip, wherein each of the one or more optical fibers is fixedly coupled to a respective port in the distal tip, and wherein a distal end of each of the one or more optical fibers terminates at the outer surface of the distal tip at each respective port in the distal tip such that the one or more optical fibers directly delivers the light energy to the tissue and collects light from the tissue at the same respective port;

illuminating the tissue through the ports in the distal tip of the catheter to excite nicotinamide adenine dinucleotide hydrogen (NADH) in an area of the tissue including ablated cardiac tissue and non-ablated tissue;

collecting light reflected from the tissue through the plurality of openings and directing the collected light to a light measuring instrument;

imaging the area of the tissue to detect NADH fluorescence of the area of the cardiac tissue; and producing a display of the imaged, illuminated tissue, the display illustrating the ablated cardiac tissue as having less fluorescence than non-ablated tissue.

15. The method of claim 14, further comprising ablating tissue with the distal tip prior to imaging the tissue.

16. The method of claim 15, further comprising ablating additional non-ablated tissue identified by distinguishing between the ablated tissue and the non-ablated tissue based on an amount of fluorescence.

17. The method of claim 14, wherein the tissue is selected from a group consisting of skeletal muscle, liver, pancreas, brain, neural tissue, spleen, breast, uterus, cervical, prostate, bladder, esophagus, lung, pulmonary, arterial, blood clot or hematologic, gastrointestinal tract, adrenals, ovaries, testicles, genitourinary, and kidney.

* * * * *